US006294185B1

United States Patent
Worley et al.

(10) Patent No.: US 6,294,185 B1
(45) Date of Patent: *Sep. 25, 2001

(54) MONOMERIC AND POLYMERIC CYCLIC AMINE AND N-HALAMINE COMPOUNDS

(75) Inventors: Shelby D. Worley; Gang Sun, both of Auburn, AL (US); Wanying Sun, Lodi, NJ (US); Tay-Yuan Chen, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/310,657

(22) Filed: Sep. 22, 1994

Related U.S. Application Data

(63) Continuation-in-part of application No. 08/282,154, filed on Jul. 28, 1994, now Pat. No. 5,490,983, which is a continuation of application No. 08/031,228, filed on Mar. 12, 1993, now abandoned.

(51) Int. Cl.[7] .................. A01N 25/00; C08F 116/00; C08F 122/40
(52) U.S. Cl. .................. 424/405; 525/326.8; 525/328.2; 525/328.6; 525/333.2; 525/333.3; 525/333.6
(58) Field of Search .............. 525/326.8, 328.2, 525/333.2, 333.3

(56) References Cited

U.S. PATENT DOCUMENTS

| | | | |
|---|---|---|---|
| 3,931,213 | 1/1976 | Kaminski et al. | 260/307 |
| 4,000,293 | 12/1976 | Kaminski et al. | 424/272 |
| 4,349,646 | 9/1982 | Nudel et al. | 525/256 |
| 4,420,590 | 12/1983 | Gartner | 525/357 |
| 4,681,948 | 7/1987 | Worley | 548/319 |
| 4,767,542 | 8/1988 | Worley | 210/755 |
| 5,057,612 | 10/1991 | Worley et al. | 548/301 |
| 5,126,057 | 6/1992 | Worley et al. | 210/755 |

OTHER PUBLICATIONS

David W. Emerson, "Slow Release of Active Chlorine and Bromine from Styrene–Divinylbenzene Copolymers Bearing N,N–dichlorosulfonamide, N–chloro–N–alkylsulfonamide, and N–bromo N–alkylsulfonamide Functional Groups. Polymer–Supported Reagents," *Ind. Eng. Chem. Res.* 30:2426–2430 (1991).

David W. Emerson, "Polymer–Bound Active Chlorine: Disinfection of Water in a Flow System. Polymer Supported Reagents," *Ind. Eng. Chem. Res.* 29:448–450 (1990).

Emerson, et al., "Functionally Modified Poly(styrene–divinylbenzene). Preparation, Characterization, and Bactericidal Action," *Ind. Eng. Chem. Res. Dev.* 17(3):269–274 (1978).

*Primary Examiner*—Jyothsna Venkat
(74) *Attorney, Agent, or Firm*—Christensen O'Connor Johnson Kindness PLLC

(57) ABSTRACT

Cyclic amine monomers and polymers and N-halamine biocidal polymer compounds are provided. Methods of making and using the same wherein the functional groups unhalogenated or halogenated hydantoins, triazine diones, imidazolidinones, and pyrimidinones are substituted onto inexpensive polymer units such as polystyrene, polyethylene, and modified polymethacrylamide are provided. The cyclic amine monomers and polymers can be utilized to form the biocidal N-halamine polymers. These N-halamine polymers are stable, insoluble biocides which release only small amounts of free halogen and other impurities. They can be useful as disinfectants for potable water, swimming pools, hot tubs, industrial water systems, cooling towers, air-conditioning systems, gas streams, paints, oils, ointments, fabrics, rubber materials, sterile bandages, coatings, hard surfaces, liners of containers, and the like.

19 Claims, No Drawings

MONOMERIC AND POLYMERIC CYCLIC AMINE AND N-HALAMINE COMPOUNDS

This application is a continuation-in-part of application Ser. No. 08/282,154, filed Jul. 28, 1994 is now U.S. Pat. No. 5,490,983, which is a continuation of application Ser. No. 08/031,228, filed Mar. 12, 1993 now abandoned. These applications are incorporated by reference in their entirety.

BACKGROUND OF THE INVENTION

1. Field of the Invention

The present invention relates to biocidal polymers for disinfection of halogen-sensitive organisms and the precursor polymers and monomers from which the biocidal polymers can be prepared. In particular, biocidal polymers of cyclic N-halamines and their precursor cyclic amine monomers and polymers are provided. Additionally provided are methods of making such monomers and polymers. The biocidal cyclic N-halamine polymers are useful for disinfection of habitats such as air and gas streams, water such as in potable water supplies, swimming pools, industrial water systems and air conditioning systems, organic fluids, hard surfaces, and elastomeric, plastic and fabric materials.

2. Background Art

Current disinfectants which are in use for purposes such as disinfecting water, as can be used in potable water supplies, swimming pools, hot tubs, industrial water systems, cooling towers, spacecraft, waste water treatment plants, air conditioning systems, military field units, camping expeditions, and in other sanitizing applications, as well as of organic fluids such as oils, paints, coatings, and preservatives, and in various medicinal applications all have serious limitations. Sources of the most commonly used disinfectant free halogen (chlorine, bromine, or iodine) are effective disinfectants, but free halogen is corrosive toward materials, toxic to marine life, reactive with organic contaminants to produce toxic trihalomethanes, irritating to the skin and eyes of humans, and relatively unstable in water, particularly in the presence of sunlight or heat. Ozone and chlorine dioxide are also effective disinfectants, but they are not persistent in water such that they have to be replenished frequently; they also may react with organic contaminants to produce products having unknown health risks. Combined halogen compounds such as the commercially employed hydantoins and cyanurates as well as the recently discovered oxazolidinones (Kaminski et al., U.S. Pat. Nos. 4,000,293 and 3,931,213) and imidazolidinones (Worley et al., U.S. Pat. Nos. 4,681,948; 4,767,542; 5,057,612; 5,126,057) are much more stable in water than are free halogen, ozone, and chlorine dioxide, but in general they require longer contact times to inactivate microorganisms than do the less stable compounds mentioned.

A characteristic which all of the aforementioned disinfectants have in common is that they are soluble to some extent in water. Thus humans or animals drinking or contacting the water are exposed to the compounds and products of their reactions with contaminants which could cause health risks in some situations.

Polymeric quaternary ammonium anionic-exchange resins have been known for many years (see for example U.S. Pat. Nos. 2,595,225; 2,923,701; 2,980,657; 2,980,634; 3,147,218; 3,288,770; 3,316,173; 3,425,790; 3,462,363; 3,554,905; 3,539,684; 3,817,860; 3,923,665; 4,187,183; 4,349,646; 4,420,590). The "polyquats" have important limitations. Most are soluble in water which means that they could pose a threat to humans or animals drinking or contacting water containing them. The insoluble polyquats tend to release fairly high concentrations of free halogen, and the most effective of these release the triiodide ion, which is undesirable with respect to dietary intake for certain groups of the population (U.S. Pat. No. 4,349,646). Such compounds are also generally expensive to manufacture.

Functionally modified poly(styrene-divinylbenzene) compounds containing N-chlorinated sulfonamide moieties have been prepared and shown to have biocidal properties (see for example Emerson et al., *Ind. Eng. Chem. Prod. Res. Dev.*, 17:269 (1978); *Ind. Eng. Chem. Res.*, 29:448 (1990); *Ind. Eng. Chem. Res.*, 30:2426 (1991)). However, these N-halamines do not contain the N—Cl or N—Br moieties in a cyclic ring and are hence not expected to be as stable toward release of free halogen as those to be described herein. In fact, they are known to release greater than 1 milligram per liter of free chlorine when the pH of water flowing through them is greater than 7.0.

Therefore, there is a great need for insoluble broad-spectrum disinfectants which kill microorganisms upon contact, but which do not leach undesirable organic contaminants into the medium to be disinfected, and which maintain a very low concentration of free halogen (less than 1 milligram per liter) in such medium. There is also a need for methods to treat many various habitats in which halogen-sensitive microorganisms dwell.

This invention solves this need by providing precursor cyclic amine polymers and precursor cyclic amine monomers, and methods for preparing them, for use in preparing biocidal polymers and copolymers such as cyclic N-halamine polymers. Also provided are methods of preparing cyclic N-halamine biocidal polymers.

SUMMARY OF THE INVENTION

The present invention relates to a cyclic amine polymer comprising a monomeric repeating unit of the structure:

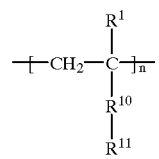

wherein $R^1$ is selected from the group consisting of hydrogen and from $C_1$ to $C_4$ alkyl; n is at least 2; $R^{10}$ is a bond or parasubstituted phenyl; and $R^{11}$ is a cyclic amine unit of a 5- to 6-membered heterocyclic ring in which the members of the ring are all selected from the group consisting of at least 3 carbon atoms, from 1 to 3 nitrogen heteroatoms, and from 0 to 1 oxygen heteroatom;

wherein $R^{10}$ is attached to a linkage carbon of $R^{11}$, wherein said linkage carbon of $R^{11}$ is a carbon located on the ring of $R^{11}$ and is substituted with a substituent selected from the group consisting of $C_1$–$C_4$ alkyl, benzyl, and alkyl-substituted benzyl;

wherein from 0 to 2 non-linkage carbon members are a carbonyl group;

wherein from 0 to 1 non-linkage carbon member is substituted with a moiety selected from the group consisting of $C_1$–$C_4$ alkyl, phenyl, alkyl-substituted phenyl, benzyl, alkyl-substituted benzyl, pentamethylene in spirosubstituted form and tetramethylene in spirosubstituted form;

or the monomeric repeating unit is of the structure:

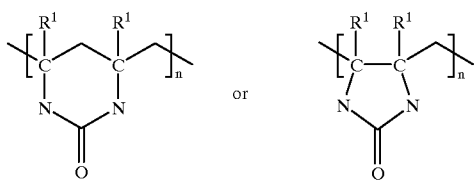

wherein $R^1$ is selected from the group consisting of hydrogen and $C_1$ to $C_4$ alkyl; and n is at least 2.

The invention additionally provides a cyclic amine monomer comprising a single mononomeric unit of the structure:

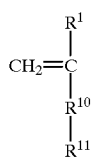

wherein $R^1$ is selected from the group consisting of hydrogen and from $C_1$ to $C_4$ alkyl; $R^{10}$ is a bond or parasubstituted phenyl; and $R^{11}$ is a cyclic amine unit of a 5- to 6-membered heterocyclic ring in which the members of the ring are all selected from the group consisting of at least 3 carbon atoms, from 1 to 3 nitrogen heteroatoms, and from 0 to 1 oxygen heteroatom;

wherein $R^{10}$ is attached to a linkage carbon of $R^{11}$, wherein said linkage carbon of $R^{11}$ is a carbon located on the ring of $R^{11}$ and is substituted with a substituent selected from the group consisting of $C_1$–$C_4$ alkyl, benzyl, and alkyl-substituted benzyl;

wherein from 0 to 2 non-linkage carbon members are a carbonyl group;

wherein from 0 to 1 non-linkage carbon member is substituted with a moiety selected from the group consisting of $C_1$–$C_4$ alkyl, phenyl, alkyl-substituted phenyl, benzyl, alkyl-substituted benzyl, pentamethylene in spirosubstituted form and tetramethylene in spirosubstituted form. The nitrogen heteroatoms in these monomers can be halogenated.

The instant invention further provides a biocidal polymer comprising a monomeric repeating unit of the structure:

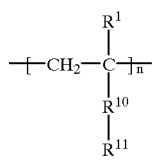

wherein $R^1$ is selected from the group consisting of hydrogen and from $C_1$ to $C_4$ alkyl; n is at least 2; $R^{10}$ is a bond or parasubstituted phenyl; and $R^{11}$ is a cyclic N-halamine unit of a 5- to 6-membered heterocyclic ring in which the members of the ring are all selected from the group consisting of at least 3 carbon atoms, from 1 to 3 nitrogen heteroatoms, and from 0 to 1 oxygen heteroatom;

wherein $R^{10}$ is attached to a linkage carbon of $R^{11}$, wherein said linkage carbon of $R^{11}$ is a carbon located on the ring of $R^{11}$ and is substituted with a substituent selected from the group consisting of $C_1$–$C_4$ alkyl, benzyl, and alkyl-substituted benzyl;

wherein from 0 to 2 non-linkage carbon members are a carbonyl group;

wherein from 0 to 1 non-linkage carbon member is substituted with a moiety selected from the group consisting of $C_1$–$C_4$ alkyl, phenyl, alkyl-substituted phenyl, benzyl, alkyl-substituted benzyl, pentamethylene in spirosubstituted form and tetramethylene in spirosubstituted form;

wherein each nitrogen heteroatom is substituted with a moiety selected from the group consisting of chlorine, bromine and hydrogen, provided that at least one such moiety is selected from the group consisting of chlorine and bromine;

or the monomeric repeating unit is of the structure:

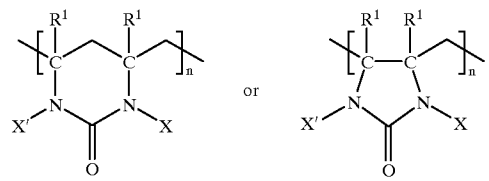

wherein $R^1$ is selected from the group consisting of hydrogen and $C_1$ to $C_4$ alkyl; n is at least 2; and X and X' are selected from the group consisting of chlorine, bromine and hydrogen, provided that at least one of X and X' is selected from the group consisting of chlorine and bromine.

The present invention additionally provides a cyclic amine copolymer comprising a monomeric repeating unit of the structure:

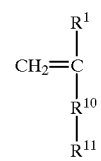

wherein $R^1$ is selected from the group consisting of hydrogen and from $C_1$ to $C_4$ alkyl; $R^{10}$ is a bond or parasubstituted phenyl; and $R^{11}$ is a cyclic amine unit of a 5- to 6-membered heterocyclic ring in which the members of the ring are all selected from the group consisting of at least 3 carbon atoms, from 1 to 3 nitrogen heteroatoms, and from 0 to 1 oxygen heteroatom;

wherein $R^{10}$ is attached to a linkage carbon of $R^{11}$, wherein said linkage carbon of $R^{11}$ is a carbon located on the ring of $R^{11}$ and is substituted with a substituent selected from the group consisting of $C_1$–$C_4$ alkyl, benzyl, and alkyl-substituted benzyl;

wherein from 0 to 2 non-linkage carbon members are a carbonyl group;

wherein from 0 to 1 non-linkage carbon member is substituted with a moiety selected from the group consisting of $C_1$–$C_4$ alkyl, phenyl, alkyl-substituted phenyl, benzyl, alkyl-substituted benzyl, pentamethylene in spirosubstituted form and tetramethylene in spirosubstituted form;

and at least one other type monomeric repeating unit.

The present invention further relates to a method of preparing a hydantoin or triazine-2,4-dione monomer comprising the steps of a) heating a poly-4-vinylacetophenone under vacuum to crack it into the corresponding monomer; and
b) converting the aceto moiety on the monomer to a hydantoin or triazine-2,4-dione moiety to form a hydantoin or triazine-2,4-dione monomer.

The present invention additionally relates to a method of preparing a cyclic amine polymer comprising the step of polymerizing the above hydantoin or triazine-2,4-dione monomer to form a polymer.

The instant invention also relates to a method of preparing a biocidal cyclic N-halamine polymer comprising the step of halogenating the above hydantoin or triazine-2,4-dione polymer with at least one halogen selected from the group consisting of chlorine and bromine.

It is an object of the present invention to provide an improved compound for disinfecting a habitat for halogen-sensitive microorganisms. Another object of the present invention is to provide novel cyclic amine monomers, cyclic amine polymers, and polymeric cyclic N-halamine biocidal compounds. An additional object is to provide novel methods of synthesizing these cyclic amine monomers, cyclic amine polymers and biocidal polymers including methods utilizing the cyclic amine monomers and polymers.

DETAILED DESCRIPTION OF THE INVENTION

The present invention may be understood more readily by reference to the following detailed description of specific embodiments and the Examples and Figures included therein.

As used in the claims, "a" can mean one or more, depending upon the context in which it is used.

As used herein, "cyclic amine unit" or "cyclic N-halamine unit" refers to a heterocyclic, monocyclic compound having a 4–7, and preferably 5–6, membered heterocyclic ring wherein the ring members are comprised of at least carbon and nitrogen provided there is at least one nitrogen heteroatom; wherein at least one carbon ring member can comprise a carbonyl group; and wherein one ring member can comprise oxygen; and wherein the balance of ring members is carbon. A "cyclic N-halamine unit" additionally includes that at least one halogen, preferably chlorine or bromine, is bonded to a nitrogen heteroatom.

A "cyclic amine monomer" or "cyclic N-halamine monomer" as used herein can comprise a monomer of the structure:

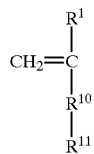

wherein $R^1$ is selected from the group consisting of hydrogen and from $C_1$ to $C_4$ alkyl; $R^{10}$ is a bond or parasubstituted phenyl; and $R^{11}$ is a cyclic amine unit of a 5- to 6-membered heterocyclic ring in which the members of the ring are all selected from the group consisting of at least 3 carbon atoms, from 1 to 3 nitrogen heteroatoms, and from 0 to 1 oxygen heteroatom;
wherein $R^{10}$ is attached to a linkage carbon of $R^{11}$, wherein said linkage carbon of $R^{11}$ is a carbon located on the ring of $R^{11}$ and is substituted with a substituent selected from the group consisting of $C_1$–$C_4$ alkyl, benzyl, and alkyl-substituted benzyl;
wherein from 0 to 2 non-linkage carbon members are a carbonyl group;
wherein from 0 to 1 non-linkage carbon member is substituted with a moiety selected from the group consisting of $C_1$–$C_4$ alkyl, phenyl, alkyl-substituted phenyl, benzyl, alkyl-substituted benzyl, pentamethylene in spirosubstituted form and tetramethylene in spirosubstituted form. The nitrogen heteroatoms can be unsubstituted or substituted with a non-halogen atom in non-halogenated monomers, or they can be substituted with a halogen, preferably chlorine or bromine, in the "N-halamine" forms of the monomer. "Halogenated" monomers or polymers as used herein can be partially or fully halogenated on the nitrogen heteroatoms.

A "polymer" as used herein can comprise two or more cyclic N-halamine monomeric repeating units or cyclic amine monomeric repeating units, and the number of monomeric repeating units in any given polymer can vary according to the use intended for the polymer. Generally, however, a preferable range of number of monomeric repeating units is from two monomers to about 5000 monomeric repeating units. Molecular weights of the polymers can vary, particularly according to the length of the polymer, substituents on the polymer, and the amount of halogenation. A preferable molecular weight range can be from about 5000 to 1 million. An even more preferable range can be from about 45,000 to about 430,000. Each cyclic N-halamine monomeric repeating unit or cyclic amine monomeric repeating unit in the polymer can be identical, but need not be. Two or more different cyclic amine monomers can be copolymerized or one or more different cyclic amine monomers can be copolymerized with one or more other suitable monomer types. Other suitable monomer types include any monomer that can be copolymerized with a herein defined cyclic amine monomer without hindering the ability of the cyclic amine monomer to be halogenated. Examples of such other monomer types include acrylonitrile, styrene, acrylamide, methacrylamide, methyl methacrylate, ethylene, propylene, butylenes, butadienes and other alkenes and dienes. "Polymer" can include copolymers and the two terms are often used interchangeably herein.

As used herein, a "habitat for halogen-sensitive microorganisms" is any substance in which or on which such organisms are capable of survival for any period of time.

Cyclic organic N-halamine compounds having two alkyl substituent groups substituted on the ring carbons adjacent to the N—Cl or N—Br moieties exhibit long-term stability in aqueous solution and release little or no free halogen, while providing adequate disinfection efficacy. Additionally, because polymeric molecules can be constructed to have low solubility in water, an insoluble cyclic N-halamine polymer containing similar cyclic N-halamine structural groups is an ideal polymeric biocide. Copolymers including cyclic N-halamine monomers can be, for example, textile fibers and elastomers (rubber materials). For example, heat-resistant unhalogenated copolymers made from cyclic amine and other polymerizable monomers can be made into fibers or elastomers which can then be made into, for example, fabric or rubber, and then halogenated to be rendered biocidal.

There are several possible strategies for incorporating cyclic N-halamine structural groups into polymers. In one, an existing cyclic amine or amide such as those described by Worley in U.S. Pat. Nos. 4,681,948; 4,767,542; 5,057,612; and 5,126,057, is functionalized with a polymerizable moiety such as a vinyl group and then polymerized to form a cyclic amine polymer. This polymer can then be halogenated. In another, and apparently preferable, strategy, an inexpensive commercial polymer is modified so as to introduce cyclic N-halamine structural groups. In yet another method, hydantoin or triazine-2,4-dione polymers are formed by cracking an acetophenone polymer made from a commercial polystyrene, by heating it under vaccum, to form monomers, converting the monomers into a hydantoin or a triazine-2,4-dione, polymerizing the monomer with the same or other monomers, and halogenating the resulting polymer or copolymer. The insoluble cyclic N-halamine polymers inactivate microorganisms upon contact, release minimal amounts of free halogen and other leachable impurities into water, and can be prepared or regenerated by, for example, passing solutions of free halogen through or contacting such solutions with the cyclic amine or amide precursor polymer material.

The cyclic amine polymers can be modified to form a desired polymer by placing substituents on the nitrogen heteroatoms on the heterocyclic amine units. For example, they can be utilized to form polymers such as the biocidal N-halamine polymers described herein. The cyclic amine polymers described herein contain heterocyclic units which can have N—H chemical bonds. These N—H bonds can be utilized to substitute other moieties to the nitrogen of the heterocyclic ring, such as halogens to create the biocidal polymers described herein.

The heterocyclic amine units can comprise from 4 to 7-membered, and preferably 5 to 6-membered, rings, wherein nitrogen is a heteroatom and oxygen can be a heteroatom, and which can have one or two carbonyl groups. The balance of atoms forming the rings are carbon. The rings can have from three to six carbon members, from one to three nitrogen heteroatoms and 0 to 1 oxygen heteroatom. A carbon atom of these heterocyclic moieties can be joined by a linkage to an additional heterocyclic amine unit by one of many possible linkages which attach to each amine unit at a single non-carbonyl carbon atom, such as a lower alkyl, i.e., a three to eleven carbon chain that can be branched when greater than three carbons, or a phenyl-lower alkyl-phenyl i.e., two phenyl groups joined by a three to eleven carbon chain that can be branched when greater than three carbons wherein one phenyl attaches to a cyclic amine unit and the other phenyl attaches to a neighboring cyclic amine unit. Additionally, the amine units can comprise a 5- or 6-membered ring having two nitrogen heteroatoms and three (for the 5-membered ring) to four (for the 6-membered ring) carbon members, one of which can be a carbonyl group, and attaching to neighboring amine units in the polymer via methylene linkages which attach to each amine unit at two of the non-carbonyl carbon ring members.

The novel N-halamine biocidal polymers described herein contain heterocyclic units which have stable N—Cl or N—Br chemical bonds necessary for biocidal action. The heterocyclic N-halamine units can comprise from 4 to 7-membered rings, and preferably 5 to 6-membered rings, wherein nitrogen is a heteroatom and oxygen can be a heteroatom, and which can have one or two carbonyl groups. The balance of the rings is carbon. The rings can have from three to six carbon members, from one to three nitrogen heteroatoms and 0 to 1 oxygen heteroatom. A carbon atom of these heterocyclic moieties can be joined by a linkage to an additional heterocyclic N-halamine unit by one of many possible linkages which attach to each N-halamine unit at a single non-carbonyl carbon atom, such as a lower alkyl, i.e., a three to eleven carbon chain that can be branched when greater than three carbons, or a phenyl-lower alkyl-phenyl i.e., two phenyl groups joined by a three to eleven carbon chain that can be branched when greater than three carbons wherein one phenyl attaches to a cyclic N-halamine unit and the other phenyl attaches to a neighboring cyclic N-halamine unit. Additionally, the N-halamine units can comprise a 5- or 6-membered ring having two nitrogen heteroatoms and three (for the 5-membered ring) to four (for the 6-membered ring) carbon members, one of which can be a carbonyl group, and attaching to neighboring N-halamine units in the polymer via methylene linkages which attach to each N-halamine unit at two of the non-carbonyl carbon ring members.

Specifically, compounds can include cyclic amine polymers comprising a monomeric repeating unit of the structure:

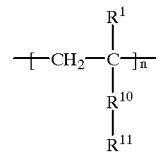

wherein $R^1$ is selected from the group consisting of hydrogen and from $C_1$ to $C_4$ alkyl; n is at least 2; $R^{10}$ is a bond or parasubstituted phenyl; and $R^{11}$ is a cyclic amine unit of a 5- to 6-membered heterocyclic ring in which the members of the ring are all selected from the group consisting of at least 3 carbon atoms, from 1 to 3 nitrogen heteroatoms, and from 0 to 1 oxygen heteroatom;

wherein $R^{10}$ is attached to a linkage carbon of $R^{11}$, wherein said linkage carbon of $R^{11}$ is a carbon located on the ring of $R^{11}$ and is substituted with a substituent selected from the group consisting of $C_1$–$C_4$ alkyl, benzyl, and alkyl-substituted benzyl;

wherein from 0 to 2 non-linkage carbon members are a carbonyl group;

wherein from 0 to 1 non-linkage carbon member is substituted with a moiety selected from the group consisting of $C_1$–$C_4$ alkyl, phenyl, alkyl-substituted phenyl, benzyl, alkyl-substituted benzyl, pentamethylene in spirosubstituted form and tetramethylene in spirosubstituted form;

or the monomeric repeating unit is of the structure:

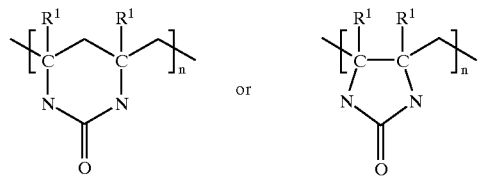

wherein $R^1$ is selected from the group consisting of hydrogen and $C_1$ to $C_4$ alkyl; and n is at least 2.

Compounds can also include biocidal cyclic N-halamine polymers wherein, in the cyclic amine polymers as described above, some or all of the nitrogen heteroatoms are substituted with a moiety selected from the group consisting of chlorine, bromine and hydrogen, provided that at least one such moiety is selected from the group consisting of chlorine and bromine.

Compounds can also include a cyclic amine copolymer comprising a monomeric repeating unit of the structure:

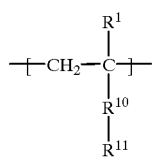

wherein $R^1$ is selected from the group consisting of hydrogen and from $C_1$ to $C_4$ alkyl; $R^{10}$ is a bond or parasubstituted phenyl; and $R^{11}$ is a cyclic amine unit of a 5- to 6-membered heterocyclic ring in which the members of the ring are all selected from the group consisting of at least 3 carbon atoms, from 1 to 3 nitrogen heteroatoms, and from 0 to 1 oxygen heteroatom;

wherein $R^{10}$ is attached to a linkage carbon of $R^{11}$, wherein said linkage carbon of $R^{11}$ is a carbon located on the ring of $R^{11}$ and is substituted with a substituent selected from the group consisting of $C_1$–$C_4$ alkyl, benzyl, and alkyl-substituted benzyl;

wherein from 0 to 2 non-linkage carbon members are a carbonyl group; benzyl, alkyl-substituted benzyl, pentamethylene in spirosubstituted form and tetramethylene in spirosubstituted form; and at least one other type monomeric repeating unit. Such other monomeric repeating units can be derived from, for example, acrylonitrile, styrene, acrylamide, methacrylamide, methyl methacrylate, ethylene, propylene, butylenes, butadienes and other alkenes and dienes. These copolymers can be halogenated, as described herein, to render them biocidal. Specifically, each nitrogen heteroatom can be substituted with a moiety selected from the group consisting of chlorine, bromine and hydrogen.

Examples of the aforedescribed amine and N-halamine compounds include, but are not limited to, the monomers and polymers represented by the repeating unit graphic formulae illustrated below:

Class 1

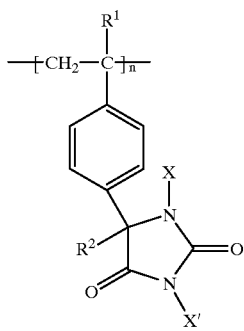

Class 2

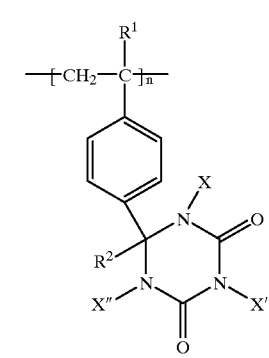

Class 3

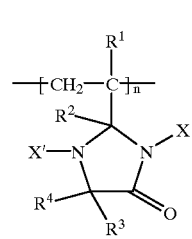

Class 4

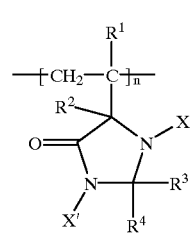

Class 5

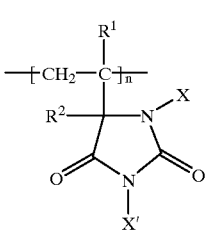

Class 6

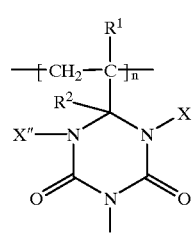

Class 7

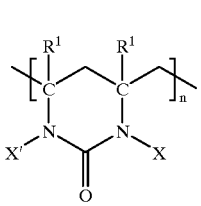

-continued

Class 8

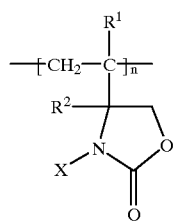

Class 9

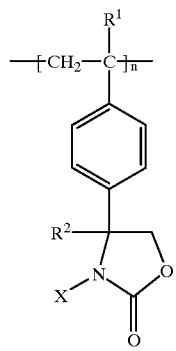

Class 10

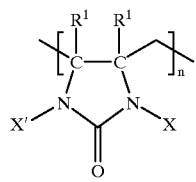

wherein in each class X, X' and X" can be hydrogen atoms; wherein $R^1$ is selected from the group consisting of hydrogen or from $C_1$ to $C_4$ alkyl; $R^2$ is selected from the group consisting of from $C_1$ to $C_4$ alkyl, benzyl, or substituted benzyl; $R^3$ and $R^4$ are selected from the group consisting of from $C_1$ to $C_4$ alkyl, phenyl, substituted phenyl, benzyl, substituted benzyl, or $R^3$ and $R^4$ may represent spirosubstitution by a component selected from the group consisting of pentamethylene and tetramethylene; or wherein in each class X, X', and X" are halogen selected from the group consisting of chlorine, bromine, and mixtures thereof, or X, X', and X" may be hydrogen provided that at least one of these is halogen selected from the group consisting of chlorine and bromine; wherein $R^1$ is selected from the group consisting of hydrogen or from $C_1$ to $C_4$ alkyl; $R^2$ is selected from the group consisting of from $C_1$ to $C_4$ alkyl, benzyl, or substituted benzyl; $R^3$ and $R^4$ are selected from the group consisting of from $C_1$ to $C_4$ alkyl, phenyl, substituted phenyl, benzyl, substituted benzyl, or $R^3$ and $R^4$ may represent spirosubstitution by a component selected from the group consisting of pentamethylene and tetramethylene.

The alkyl substituents representing $R^1$, $R^2$, $R^3$, and $R^4$ or those attached to phenyl or benzyl may contain from 1 to 4 carbon atoms, including methyl, ethyl, propyl, isopropyl, n-butyl, isobutyl, secondary butyl, and tertiary butyl.

Examples of the aforedescribed compounds for each class of cyclic amine polymer include but are not limited to: 1: poly-5-methyl-5-(4'-vinylphenyl)hydantoin; poly-5-methyl-5-(4'-isopropenylphenyl)hydantoin; 2: poly-6-methyl-6-(4'-vinylphenyl)-1,3,5-triazine-2,4-dione; poly-6-methyl-6-(4'-isopropenylphenyl)-1,3,5-triazine-2,4-dione; 3: poly-2,5,5-trimethyl-2-vinyl-1,3-imidazolidin-4-one; 4: poly-2,2,5-trimethyl-5-vinyl-1,3-imidazolidin-4-one; 5: poly-5-methyl-5-vinylhydantoin; 6: poly-6-methyl-6-vinyl-1,3,5-triazine-2,4-dione; 7: poly-(4-methylene-6-yl)-4,6-dimethyl-3,4,5,6-tetrahydro(1H)pyrimidin-2-one; 8: poly-4-methyl-4-vinyl-2-oxazolidinone; 9: poly-4-methyl-4-(4'-vinylphenyl)-2-oxazolidinone. Polymers such as these can be used to prepare halogenated biocidal polymers.

Examples of precursor cyclic amine monomers as described herein include the monomers of the herein exemplified cyclic amine polymers.

Examples of the aforedescribed compounds for each class of biocidal cyclic N-halamine polymer include but are not limited to: 1: poly-1,3-dichloro-5-methyl-5-(4'-vinylphenyl)hydantoin; poly-1,3-dichloro-5-methyl-5-(4'-isopropenylphenyl)hydantoin; poly-1-chloro-5-methyl-5-(4'-vinylphenyl)hydantoin; poly-1-chloro-5-methyl-5-(4'-isopropenylphenyl)hydantoin; poly-1,3-dibromo-5-methyl-5-(4'-vinylphenyl)hydantoin; poly-1,3-dibromo-5-methyl-5-(4'-isopropenylphenyl)hydantoin; poly-1-bromo-3-chloro-5-methyl-5-(4'-vinylphenyl)hydantoin and poly-1-bromo-3-chloro-5-methyl-5-(4'-isopropenylphenyl)hydantoin; 2: poly-1,3,5-trichloro-6-methyl-6-(4'-vinylphenyl)-1,3,5-triazine-2,4-dione; poly-1,3,5-trichloro-6-methyl-6-(4'-isopropenylphenyl)-1,3,5-triazine-2,4,-dione; poly-1,5-dichloro-6-methyl-6-(4'-vinylphenyl)-1,3,5-triazine-2,4-dione; poly-1,5-dichloro-6-methyl-6-(4'-isopropenylphenyl)-1,3,5-triazine-2,4-dione; poly-1,3,5-tribromo-6-methyl-6-(4'-vinylphenyl)-1,3,5-triazine-2,4-dione; poly-1,3,5-tribromo-6-methyl-6-(4'-isopropenylphenyl)-1,3,5-triazine-2,4-dione; poly-1-bromo-3,5-dichloro-6-methyl-6-(4'-vinylphenyl)-1,3,5-triazine-2,4-dione; and poly-1-bromo-3,5-dichloro-6-methyl-6-(4'-isopropenylphenyl)-1,3,5-triazine-2,4-dione; 3: poly-1,3-dichloro-2,5,5-trimethyl-2-vinyl-1,3-imidazolidin-4-one; 4: poly-1,3-dichloro-2,2,5-trimethyl-5-vinyl-1,3-imidazolidin-4-one; 5: poly-1,3-dichloro-5-methyl-5-vinylhydantoin; poly-1-chloro-5-methyl-5-vinylhydantoin; poly-1,3-dibromo-5-methyl-5-vinylhydantoin; and poly-1-bromo-3-chloro-5-methyl-5-vinylhydantoin; 6: poly-1,3,5-trichloro-6-methyl-6-vinyl-1,3,5-triazine-2,4-dione; 7: poly-1,3-dichloro-(4-methylene-6-yl)-4,6-dimethyl-3,4,5,6-tetrahydro(1H)pyrimidin-2-one; poly-1-chloro-(4-methylene-6-yl)-4,6-dimethyl-3,4,5,6-tetrahydro(1H)pyrimidin-2-one; poly-1,3-dibromo-(4-methylene-6-yl)-4,6-dimethyl-3,4,5,6-tetrahydro(1H)pyrimidin-2-one; and poly-1-bromo-3-chloro-(4-methylene-6-yl)-4,6-dimethyl-3,4,5,6-tetrahydro(1H)pyrimidin-2-one; 8: poly-3-chloro-4-methyl-4-vinyl-2-oxazolidinone; and 9: poly-3-chloro-4-methyl-4-(4'-vinylphenyl)-2-oxazolidinone.

By substitution of other named substituents for $R^1$, $R^2$, $R^3$, and $R^4$, e.g., ethyl, propyl, phenyl, etc., for one or more of the derivatives above named, other correspondingly named N-halo or unhalogenated derivatives may be formed.

The polymeric cyclic N-halamine biocidal compounds of the present invention can be prepared by reacting the corresponding unhalogenated polymers, herein referred to as "cyclic amine polymers[s]" or "precursor cyclic amine polymer[s]," with a source of chlorine, bromine, or in the case of the mixed bromochloro derivatives, first a source of bromine and then a source of chlorine or the reverse. While chlorine gas or liquid bromine may be utilized, other milder halogenating agents such as calcium hypochlorite, sodium hypochlorite, N-chlorosuccinimide, N-bromosuccinimide, sodium dichloroisocyanurate, trichloroisocyanuric acid, tertiary butyl hypochlorite, N-chloroacetamide, N-chloramines, N-bromamines, etc., can also be employed.

Halogenation of the unhalogenated polymers can be accomplished in aqueous media or in mixtures of water with common inert organic solvents such as methylene chloride, chloroform, and carbon tetrachloride, or in inert organic solvents themselves, at room temperature. The precursor cyclic amine polymer can be a previously-utilized cyclic N-halamine polymer that has become ineffective at killing microorganisms due to inactivation of the N—Cl or N—Br moieties. The above-described halogenations can be performed in situ, if desired. In general, the longer the halogenation reaction occurs, the more likely the polymers are to be fully halogenated. However, "halogenating" or "halogenated" as used herein includes partially as well as fully halogenated. Preferred halogens are chlorine and bromine.

The unhalogenated precursor cyclic amine polymers described in this invention can be prepared from existing inexpensive commercial grade polymers. In the case of the structure represented above by class 1, commercial grade polystyrene or substituted polystyrenes can be reacted with acetyl chloride or acetic anhydride in the presence of aluminum trichloride as a catalyst in common solvents such as carbon disulfide, methylene chloride, carbon tetrachloride, excess acetyl chloride, or nitrobenzene in a Friedel Crafts acylation to produce a para-acylated polystyrene, followed by reaction with potassium cyanide and ammonium carbonate in common solvents such as ethanol or ethanol/water mixtures, acetamide, dimethylformamide, dimethylacetamide, or 1-methyl-2-pyrolidinone to produce the poly-5-methyl-5-(4'-vinylphenyl)hydantoin. For the structure represented by class 2, the same acylated polystyrene or substituted polystyrenes as for the class 1 structure can be reacted with dithiobiuret in the presence of dry hydrogen chloride in a dioxane/ethanol solvent followed by oxidation of the dithione produced with hydrogen peroxide in the presence of sodium hydroxide to produce the poly-6-methyl-6-(4'-vinylphenyl)-1,3,5-triazine-2,4-dione. For the structure represented by class 3, poly-alkylvinyl ketone can be reacted with ammonium sulfide and an appropriate dialkyl cyanohydrin in a solvent such as dioxane, tetrahydrofuran, chloroform, or methylene chloride to produce a poly-vinyl-1,3-imidazolidine-4-thione which can then be directly chlorinated in aqueous sodium hydroxide to produce the poly-1,3-dichloro-2-vinyl-1,3-imidazolidin-4-one. For the structure represented by class 4, poly-alkyl vinyl ketone can be reacted with sodium cyanide in the presence of sulfuric acid and then ammonium sulfide and an appropriate ketone in a solvent such as dioxane. The poly-vinyl thione product obtained can then be directly chlorinated in aqueous sodium hydroxide to produce the poly-1,3-dichloro-5-vinyl-1,3-imidazolidin-4-one. For the structure represented by class 5, poly-alkyl vinyl ketone can be reacted with potassium cyanide and ammonium carbonate in solvent containing dioxane, ethanol, and water to produce a poly-5-alkyl-5-vinylhydantoin. For the structure represented by class 6, poly-alkyl vinyl ketone can be reacted with dithiobiuret in the presence of hydrochloric acid followed by oxidation with hydrogen peroxide in the presence of sodium hydroxide to produce a poly-6-alkyl-6-vinyl-1,3,5-triazine-2,4-dione. For the structure represented by class 7, polymethacrylamide can be reacted with bromine in the presence of sodium hydroxide in a Hofmann degradation to produce a poly-diamine which can be reacted further with phosgene in the presence of toluene, water, and sodium hydroxide to produce poly-(4-methylene-6-yl)-4,6-dimethyl-3,4,5,6-tetrahydro(1H)pyrimidine-2-one.

For the structure represented by class 8, the monomer 4-methyl-4-vinyl-2-oxazolidinone obtained by reaction of phosgene with 2-amino-2-methyl-3-buten-1-ol can be polymerized and the resulting polymer then chlorinated in aqueous alkaline solution to produce the poly-3-chloro-4-methyl-4-vinyl-2-oxazolidinone. For the structure represented by class 9, the monomer 4-methyl-4-(4'-vinylphenyl)-2-oxazolidinone obtained by reaction of phosgene with 2-amino-2-(4'-vinylphenyl)-1-propanol can be polymerized and the resulting polymer then chlorinated in aqueous alkaline solution to produce the poly-3-chloro-4-methyl-4-(4'-vinylphenyl)-2-oxazolidinone.

A hydantoin or triazine-2,4-dione monomer of the present invention can also be made by heating a poly-4-vinylacetophenone under vacuum to crack it into the corresponding monomer; and converting the aceto moiety on the monomer to a hydantoin or triazine-2,4-dione moiety to form a hydantoin or triazine-2,4-dione monomer. Specifically, the cyclic amine monomers represented herein by classes 1 and 2 can be prepared by acylating a polystyrene or an α-substituted polystyrene to form a poly-4-vinylacetophenone and then cracking the poly-4-vinylacetophenone to its corresponding monomers by heating the polymers under vacuum. Any poly-4-vinylacetophenone can be utilized in this method wherein the vinyl carbon linked to the acetophenone is unsubstituted (e.g., poly-4-vinylacetophenone) or is substituted with from $C_1$ to $C_4$ alkyl (e.g., poly-4-isopropenylacetophenone when this vinyl carbon is substituted with a methyl group). The starting poly-4-vinylacetophenone also includes polymers wherein the carbonyl carbon at the aceto moiety is substituted with from $C_1$ to $C_4$ alkyl, benzyl or substituted benzyl (this substituent is $R^2$ in the final product). Heating of the acetophenone polymers can be done at any temperature capable of, under vacuum, cracking the polymers to their corresponding monomers. Preferred temperature ranges include from about 300° C. to about 800° C. The heating process can be done under a vacuum that allows cracking of the polymers while heating. Generally, a low vacuum is preferred. Preferred vacuum conditions range from about 0.1 Torr to about 50 Torr.

The aceto moiety on the resulting acetophenone monomers, e.g., 4-vinylacetophenone or 4-isopropenylphenone, can then be converted into a hydantoin or a triazine-2,4-dione. By "converted" is meant that the aceto moiety, in the conversion reaction, becomes a part of a hydantoin ring or a triazine-2,4-dione ring that is attached to the phenyl group originating from the acetophenone. For example, to form a hydantoin, the acetophenone monomer can be reacted with potassium cyanate and ammonium carbonate in common solvents such as ethanol or ethanol/water mixtures, acetamide, dimethylformamide, dimethylacetamide, or 1-methyl-2-pyrolidinone to produce a hydantoin monomer. Alternatively, a triazine-2,4-dione monomer can be formed by, for example, reacting the acetophenone monomer with dithiobiuret in a dioxane/ethanol solvent in the presence of dry hydrogen chloride gas (to produce a dithione), followed by oxidation with hydrogen peroxide in the presence of sodium hydroxide. The resulting hydantoin or triazine-2,4-dione can include derivatives such as substituted hydantoin or substituted triazine-2,4-dione.

The resulting hydantoin or triazine-2,4-dione monomers can then be polymerized to form a cyclic amine polymer. Polymerization can be done by, for example, a free radical initiation method, as is known in the art. For example, one can dissolve the monomers in absolute ethanol or other suitable solvent and react this solution, at the boiling point for the solvent, with azobisisobutyronitrile under nitrogen atmosphere to produce the unhalogenated cyclic amine polymer. Alternatively, the monomers can be copolymerized with other types of monomer by a free radical initiation method, such as by dissolving all desired monomers in N,N-dimethylacetamide or other suitable solvent and adding, under nitrogen atmosphere, azobisisobutyronitrile, and allowing the mixture to react, at the boiling point temperature for the solvent, under nitrogen atmosphere to produce the copolymer. The other monomers copolymerized with the cyclic amine monomers can be, but are not limited to, other cyclic amine monomers. For example, other monomer types that can be copolymerized with one or more herein described cyclic amine monomers can include acrylonitrile, styrene, methacrylamide, methylmethacrylate, ethylene, propylene, butylenes, butadienes and other alkenes and dienes. The resulting unhalogenated polymers or copolymers can then be halogenated, such as with free chlorine and bromine sources, as described herein. Additionally, the cyclic amine monomers can be halogenated.

The polymeric cyclic N-halamine biocidal compounds are insoluble in water and in most known organic solvents. They can be employed as disinfectants against undesirable microorganisms in many habitats including aqueous as well as other solution media, semi-solid media, surfaces of materials and in gas streams by treating the media or material with a biocidally effective amount of polymer compound. An aqueous medium can include, for example, that as found in potable water sources, swimming pools, hot tubs, industrial water systems, cooling towers, air conditioning systems, waste disposal units and the like. As used herein, a "liquid or semi-solid medium" includes liquid or semi-solid media in which halogen-sensitive microorganisms can dwell, which can include, paint, wax, household cleaners, wood preservatives, oils, ointments, douches, enema solutions and the like. As used herein, a "surface" can include any surface upon which halogen-sensitive microorganisms can dwell and to which a claimed polymer can be bound, which can include surfaces of, for example, textile fabric, metal, rubber, concrete, wood, glass and bandaging. As used herein, "a gaseous medium" includes any gas in which halogen-sensitive microorganisms can dwell, such as air, oxygen, nitrogen, or any other gas, such as found in air handling systems in, for example, enclosed bunkers, vehicles, hospitals, hotels, convention centers or other public buildings.

For aqueous, liquid or gas media, disinfection is best done by flowing microbiologically contaminated water or gas, e.g. air, over or through the solid polymer in an enclosed column or cartridge or other type filter. The residence time of the contaminated substance in the filter unit will determine the efficacy of disinfection. For disinfection applications involving paints, coatings, preservatives and semi-solid media, the polymeric compounds are best introduced as fine suspensions in the base materials to be disinfected. These polymeric biocides can be incorporated into textile fibers, rubber materials, and solid surfaces as well to serve as biological preservatives. This can be effected as blends or by copolymerization of the monomers of the cyclic amines with other known polymerizable materials.

Once a filter unit becomes ineffective at killing microorganisms due to inactivation of the N—Cl or N—Br moieties, it can be regenerated by passing an aqueous solution of free halogen through it. Additionally, the cyclic N-halamine polymer biocide can be created or regenerated in situ by adding a stoichiometric amount of free halogen, either chlorine or bromine, to a precursor cyclic amine polymer contained in a material such as in a filter unit, in paint, oil, textile fabric or the like, or bound to a surface of a material such as wood, glass, plastic polymer coating, textile fabric, metal, rubber, concrete, cloth bandage or the like.

Thus, also, the unhalogenated precursor cyclic amine polymer can be incorporated into a material, surface, or filter unit as described above, and this polymer can then later, at an advantageous time, be halogenated in situ to render it biocidal.

The cyclic N-halamine biocidal polymers described herein can also be employed together with sources of active disinfecting halogen such as free chlorine or bromine or the various N-halamine sources of the same. The polymers liberate very little free halogen themselves, generally less than 1 milligram per liter of water for the N-chloro polymers, and they can be used, in fact, to abstract larger amounts of free halogen from water flowing through them. They can serve as a source of small amounts of free halogen residual (less than 1 milligram per liter for the N-chloro polymers) for disinfection applications.

All microorganisms in aqueous or other solutions or on hard surfaces susceptible to disinfection by free halogen, e.g. free chlorine, or combined halogen, e.g. N-haloimidazolidinones, N-halooxazolidinones, N-halohydantoins, N-haloisocyanurates, etc., will also be susceptible to disinfection by the biocidal polymer compounds of this invention. Such microorganisms include, for example, bacteria, protozoa, fungi, viruses and algae.

The biocidal polymers described herein can be employed in a variety of disinfecting applications. They will be of importance in controlling microbiological contamination in cartridge or other type filters installed in the recirculating water systems of remote potable water treatment units, swimming pools, hot tubs, air conditioners, and cooling towers, as well as in recirculating air-handling systems used in military bunkers and vehicles and in civilian structures. For example, the halogenated polymers will prevent the growth of undesirable organisms, such as the bacteria genera Staphylococcus, Pseudomonas, Salmonella, Shigella, Legionella, Methylobacterium, Klebsiella, and Bacillus; the fungi genera Candida, Rhodoturula, and molds such as mildew; the protozoa genera Giardia, Entamoeba, and Cryptosporidium; the viruses poliovirus, rotavirus, HIV virus, and herpesvirus; and the algae genera Anabaena, Oscillatoria, and Chlorella; and sources of biofouling in closed-cycle cooling water systems. They will be of importance as preservatives and preventatives against microbiological contamination in paints, coatings, and on surfaces. They will be of particular importance to the medical field for use in ointments, bandages, sterile surfaces, condoms, surgical gloves, and the like, and for attachment to liners of containers used in the food processing industry. They can be used in conjunction with textiles for sterile applications, such as coatings on sheets or bandages used for burn victims or on microbiological decontamination suits.

The halogenated polymers described herein can be used in diverse liquid and solid formulations such as powders, granular materials, solutions, concentrates, emulsions, slurries, and in the presence of diluents, extenders, fillers, conditioners, aqueous solvent, organic solvents, and the like. Of particular use can be their employment in formulations involving wetting, emulsifying, or dispersing agents such as sulfonates, alcohols, or similar surface active materials. The compounds are also compatible with buffering agents and other sources of halogen.

The present invention is more particularly described in the following examples which are intended as illustrative only since numerous modifications and variations therein will be apparent to those skilled in the art.

EXAMPLES

Example 1

Preparation of poly-1,3-dichloro-5-methyl-5-(4'-vinylphenyl)hydantoin (1a)

To a three-neck flask equipped with dropping funnel, reflux condenser, and mechanical stirrer was added, in order, 600 milliliters of carbon disulfide, 160.2 grams (1.2 moles) of aluminum chloride, 64.2 milliliters (0.90 mole) of acetyl chloride, and a solution of 62.4 grams (0.6 mole of repeating unit) of commercial-grade polystyrene (Aldrich Chemical Co., Milwaukee, Wis.) in 600 additional milliliters of carbon disulfide. The polystyrene was reported by the manufacturer to have an average molecular weight of 280,000; samples having average molecular weights of 45,000 and 430,000 have also been employed successfully also. A vigorous chemical reaction occurred, causing the carbon disulfide solvent to begin to reflux at room temperature. The mixture was then refluxed for 2 hours using a heated water bath as a source of heat. Most of the carbon disulfide was removed by distillation, and the semi-solidified mixture was added to 600 milliliters of an ice/hydrochloric acid mixture (2 parts ice by weight, 1 part hydrochloric acid by weight) in order to decompose the poly-4-vinylacetophenone/aluminum chloride complex which had formed. The desired product poly-4-vinylacetophenone precipitated from the mixture as a pale yellow solid. The product was recovered by suction filtration and then purified by exposure to 600 milliliters of boiling 1 normal sodium hydroxide solution for 15 minutes followed by suction filtration to recover the product. Then the product was further purified by exposure to 600 milliliters of boiling water for 15 minutes followed by suction filtration. This latter step was repeated 3 more times. The final purified poly-4-vinylacetophenone was dried at room temperature. 86.0 grams of light yellow solid product resulted which was 98% of the yield theoretically expected. The product was found to be soluble at room temperature in a mixture having 3 parts dioxane/1 part ethanol or in dioxane itself at elevated temperature. The product exhibited prominent infrared absorption bands in a KBr pellet at 1604 and 1684 $cm^{-1}$.

3.65 grams (0.025 mole) of the poly-4-vinylacetophenone prepared as described above, 4.5 grams (0.07 mole) of potassium cyanide, and 100 grams of acetamide as a solvent were mixed together in a 300 milliliter glass liner. The liner containing the mixture was placed in a Parr model 4841 300-milliliter high-pressure reactor (Parr Instrument Co., Moline, Ill.) and stirred for 30 minutes at a temperature of 150° C. The mixture was cooled to 80° C., and 14.4 grams (0.15 mole) of ammonium carbonate was added. The reactor was resealed, and the mixture was stirred at a temperature of 150° C. for 20 hours. The pressure was released from the reactor at 100° C., and the product was mixed with 500 milliliters of water. The crude poly-5-methyl-5-(4'-vinylphenyl)hydantoin precipitated as a pale yellow solid and was recovered by suction filtration. The product was purified by washing with six 500 milliliter portions of near boiling water, and then was dried at room temperature to yield 5.2 grams of light yellow powder which was 96% of the yield expected theoretically. The polymer was found to swell in 1 normal sodium hydroxide and in the organic solvents dimethyl sulfoxide, dimethyl formamide, trifluoroacetic acid, and 1-fluoro-2,4-dinitrobenzene, but it was not soluble in any solvent which was attempted. An elemental analysis of the product gave the following results: (calculated/found) % carbon 66.67/62.21,% hydrogen 5.56/6.00, and % nitrogen 12.96/11.71. The product exhibited prominent infrared bands in a KBr pellet at 1718, 1772, and 3262 $cm^{-1}$.

5.0 grams (0.023 mole) of the poly-5-methyl-(4'-vinylphenyl)hydantoin prepared as described above was suspended in 100 milliliters of 1 normal sodium hydroxide (0.1 mole) in a 250 milliliter two-neck flask. The flask containing the mixture was placed in an ice bath, and the temperature was held below 10° C. while chlorine gas was bubbled in. The reaction was continued until the pH of the mixture became 7.0. The desired product poly-1,3-dichloro-5-methyl-5-(4'-vinylphenyl)hydantoin (1a) precipitated as a white solid from the mixture and was recovered by suction filtration. The product was washed with distilled, deionized water until no free chlorine could be detected by iodometric titration. Following drying, the product yield was 6.0 grams or 92% of that theoretically expected. The polymer was found to swell in 1 normal sodium hydroxide solution and in the organic solvents dimethyl sulfoxide, 1-methyl-2-pyrolidinone, dioxane, dimethyl formamide, hexamethylphosphoramide, cyclohexanone, trifluoroacetic acid, 1-fluoro-2,4-dinitrobenzene, and hexafluoroisopropyl alcohol, but it was not soluble in any solvent attempted. An elemental analysis of the product gave the following results: (calculated/found) % carbon 50.53/51.04,% hydrogen 3.51/3.86, % nitrogen 9.82/8.98, and % chlorine 24.91/24.57. The product yielded prominent infrared bands in a KBr pellet at 1757 and 1807 $cm^{-1}$.

Example 2

Preparation of poly-1,3-dichloro-5-methyl-5-(4'-isopropenylphenyl)hydantoin (1b)

A Friedel-Crafts acylation was performed on a commercial sample of poly-α-methylstyrene (Aldrich Chemical Co., Milwaukee, Wis.) having average molecular weight as stated by the manufacturer of 93,000. The procedure employed was identical to that discussed in Example 1. The yield of poly-4-isopropenylacetophenone was 94% of that theoretically expected. The product exhibited prominent infrared bands in a KBr pellet at 1601 and 1682 $cm^{-1}$.

The polyacetophenone was then reacted with potassium cyanide and ammonium carbonate in acetamide solvent in the same manner as discussed in Example 1. The yield of poly-5-methyl-5-(4'-isopropenylphenyl)hydantoin was 77% of that theoretically expected, and infrared analysis showed prominent bands in a KBr pellet at 1716, 1772, and 3221 $cm^{-1}$. It was soluble in organic solvents such as dimethyl sulfoxide. $^{13}C$ NMR (DMSO-$d_6$) δ=26, 64, 132–136, 146, 156, 177; $^1H$ NMR (DMSO-$d_6$) δ=8.55 (1H), 10.72 (1H).

Chlorination of the above sample in a manner analogous to that discussed in Example 1 then produced poly-1,3-dichloro-5-methyl-5-(4'-isopropenylphenyl)hydantoin (1b) in 83% yield with prominent infrared bands in a KBr pellet at 1327, 1755, and 1805 $cm^{-1}$.

Example 3

Preparation of poly-1,3,5-trichloro-6-methyl-6-(4'-vinylphenyl)-1,3,5-triazine-2,4-dione (2a)

1.46 grams (0.01 mole of repeating unit) of poly-4-vinylacetophenone, prepared as described in Example 1 for a low molecular weight commercial poly-styrene (45,000)

was dissolved in a mixture of 30 milliliters of dioxane and 10 milliliters of ethanol and placed in a 100 milliliter two-neck flask. Then 1.35 grams (0.01 mole) of dithiobiuret was added to the mixture in the flask while stirring. The dry hydrogen chloride gas generated by slowly dropping 10 milliliters of concentrated hydrochloric acid into 20 milliliters of concentrated sulfuric acid in a separate vessel was slowly bubbled into the flask containing the reaction mixture over a 1 hour time period. The flask was then sealed, and the mixture was stirred for 15 hours. The solid product which resulted was dissolved in 200 milliliters of 2 normal sodium hydroxide, and the remaining solid residue which had less percentage conversion of the ketone to the triazine thione was removed by suction filtration. The filtrate containing the desired product was neutralized with glacial acetic acid. The desired poly-6-methyl-6-(4'-vinylphenyl)-1,3,5-triazine-2,4-dithione precipitated as a white solid and was recovered by suction filtration. The product was purified by washing twice with 100 milliliter portions of distilled water and drying at room temperature. The purified product yield was 1.20 grams or 46% of that expected theoretically. It exhibited prominent infrared bands in a KBr pellet at 1541, 1604, and 3194 cm$^{-1}$; $^1$H NMR (DMSO-d$_6$) δ=10.71 (2H), 11.27 (1H). The combined yield of the purified product and the solid containing partial conversion of the ketone to the triazine thione was 1.74 grams, or 66% of that expected theoretically.

2.11 grams (0.008 mole) of the purified poly-thione product prepared as described above was dissolved in 50 milliliters of 2 normal sodium hydroxide in a 100 milliliter flask. While stirring the contents of the flask, and maintaining the temperature below 40° C. by use of an external cold water bath, 9.2 grams (0.08 mole) of 30% hydrogen peroxide was slowly added. Then the mixture was heated briefly to 80° C. to decompose any excess hydrogen peroxide, and then neutralized with 2 normal sulfuiric acid to produce a yellow solid product. The product poly-6-methyl-6-(4'-vinylphenyl)-1,3,5-triazine-2,4-dione was recovered by suction filtration, washed with 100 milliliters of distilled water, and dried at room temperature. The yield was 1.65 grams or 89% of that expected theoretically. Analysis of the product by infrared spectroscopy showed prominent bands in a KBr pellet at 1709 and 3244 cm$^{-1}$; $^1$H NMR (DMSO-d$_6$) δ=8.54 (2H); 9.31 (1H).

Then 1.0 gram (0.0043 mole) of the poly-dione product prepared as described above was suspended in 100 milliliters of 1 normal sodium hydroxide in a 250 milliliter two-neck flask. The stirred mixture was maintained at a temperature lower than 10° C. while chlorine gas was slowly bubbled in until the pH reached 7.0. The product precipitated as a light yellow solid and was recovered by suction filtration. The product was purified by washing with three 100 milliliter portions of distilled-deionized water, and dried at room temperature. The yield of poly-1,3,5-trichloro-6-methyl-6-(4'-vinylphenyl)-1,3,5-triazine-2,4-dione (2a) was 1.12 grams or 71% of that expected theoretically. Infrared analysis in a KBr pellet yielded prominent bands at 1604 and 1732 cm$^{-1}$.

Example 4

Preparation of poly-1,3,5-trichloro-6-methyl-6-(4'-isopropenylphenyl)-1,3,5-triazine-2,4-dione (2b)

Poly-4-isopropenylacetophenone prepared as described in Example 2 was reacted with dithiobiuret in the presence of dry hydrogen chloride, and the product purified, in the same manner as described in Example 3. The product yield of poly-6-methyl-6-(4'-isopropenylphenyl)-1,3,5-triazine-2,4-dithione was 75.3% of that expected theoretically, and infrared analysis yielded prominent bands in a KBr pellet at 1554, 1604, and 3181 cm$^{-1}$; $^1$H NMR (DMSO-d$_6$) δ=10.74 (2H), 11.40 (1H). This product was then oxidized with hydrogen peroxide in sodium hydroxide solution as described in Example 3 to produce poly-6-methyl-6-(4'-isopropenylphenyl)-1,3,5-triazine-2,4-dione in essentially quantitative yield. The purified product exhibited prominent infrared bands in a KBr pellet at 1711 and 3246 cm$^{-1}$; $^1$NMR (DMSO-d$_6$) δ=8.52 (2H), 9.30 (1H). Chlorination of this product in 1 normal sodium hydroxide as described in Example 3, and then purification, provided the final product poly-1,3,5-trichloro-6-methyl-6-(4'-isopropenylphenyl)-1,3, 5-triazine-2,4-dione (2b) in 67% yield with prominent infrared bands in a KBr pellet at 1354 and 1732 cm$^{-1}$.

Example 5

Preparation of poly-1,3-dichloro-2,5,5-trimethyl-2-vinyl-1,3-imidazolidin-4-one (3)

Poly-methyl vinyl ketone was prepared from methyl vinyl ketone using the method described by Mark et al., in *Encyclopedia of Polymer Science and Engineering,* Wiley & Sons, New York, 17:548–567 (1989). Commercial poly-methyl vinyl ketone (Aldrich Chemical Co., Milwaukee, Wis.) can be used as well. 3.5 grams (0.05 mole of repeating unit) of the poly-methyl vinyl ketone was dissolved in 25 milliliters of dioxane in a 100 milliliter flask. Then 17 grams (0.05 mole) of 21.2% ammonium sulfide and 4.25 grams (0.05 mole) of acetone cyanohydrin were added, the flask was sealed with a glass stopper, and it was held at 60° C. with stirring for 5 hours. A precipitate resulted which was isolated by decantation and added to 300 milliliters of distilled water. The product was then removed by suction filtration and washed with 3 portions of near boiling water. Concentration of the remaining contents of the reaction flask yielded additional solid product which was also washed with 3 portions of near boiling water. The total yield of the combined solid product portions was 6.0 grams or 76% of the product poly-2,5,5-trimethyl-2-vinyl-1,3-imidazolidine-4-thione theoretically expected. However, infrared spectroscopy and $^{13}$C NMR spectroscopy both indicated the presence of unreacted carbonyl moieties indicating that some acetyl groups were not converted to the imidazolidine-4-thione ring. The estimated conversion was about 50%. Prominent infrared bands for the product in a KBr pellet occurred at 1172, 1379, 1498, 1697, and 3218 cm$^{-1}$; $^{13}$C NMR (DMSO-d$_6$): δ=21, 22–40, 73, 74, 81, 82, 176, 206, 210.

8.5 grams of the product prepared as described above was dissolved in 200 milliliters of 3 normal sodium hydroxide in a 250 milliliter flask. Chlorine gas was bubbled into the mixture while stirring at temperatures less than 10° C. until the pH reached 7.0. Then 100 milliliters of distilled water was added to the flask which was sealed and allowed to stand overnight at room temperature. The solid product that resulted was removed by suction filtration and washed with distilled, deionized water until no free chlorine could be detected using potassium iodide as an indicator in the filtrate. After drying in air, 9.7 grams of poly-1,3-dichloro-2,5,5-trimethyl-2-vinyl-1,3-imidazolidin-4-one (3) resulted (85% yield based on complete conversion of precursor polymer; the estimated conversion based on 50% conversion of the precursor polymer was 71%. The product was not soluble in water, acetone, chloroform, ethanol, diethyl ether, benzene, or ethyl acetate, but it was soluble in dimethyl sulfoxide, dimethyl formamide, and 3 normal sodium hydroxide. It exhibited prominent infrared bands in a KBr pellet at 1190, 1383, 1734, and 2943 cm$^{-1}$.

Example 6

Preparation of poly-1,3-dichloro-2,2,5-trimethyl-5-vinyl-1,3-imidazolidin-4-one (4)

1.7 grams (0.024 mole) of poly-methyl vinyl ketone prepared as described in Example 5 was dissolved in 13 milliliters of dioxane and mixed with 1.22 grams (0.025 mole) of sodium cyanide in 3 milliliters of water in a 100 milliliter flask. Then 5 grams of 40% sulfuric acid solution was added slowly with stirring while maintaining the temperature below 15° C. with an ice bath. Following addition of the sulfuric acid, the mixture was stirred for 30 additional minutes at 15° C., and then 8.5 grams (0.026 mole) of 21.2% ammonium sulfide and 1.5 grams (0.026 mole) of acetone were added at room temperature. The flask was sealed and the mixture was held at 55–60° C. with stirring for 5 hours. The mixture was cooled to room temperature and poured into 400 milliliters of distilled water. The resulting light yellow precipitate was removed by suction filtration and washed with 5 portions of near boiling water. 3.04 grams of final product, poly-2,2,5-trimethyl-5-vinyl-1,3-imidazolidine-4-thione, was obtained after drying in air. This represented a 60% yield assuming complete conversion to the poly-thione. However, infrared and $^{13}$C NMR evidence showed that some acetyl groups were unreacted; the estimated conversion was 54%. Prominent infrared bands for the product in a KBr pellet occurred at 1155, 1244, 1379, 1458, 1678, 2936 and 3252 cm$^{-1}$; $^{13}$C NMR (DMSO-d$_6$): δ=21, 40, 176, 206, 210.

1.28 grams of the product prepared as described above was chlorinated in the same manner as was the poly-thione of Example 5. 1.47 grams of poly-1,3-dichloro-2,2,5-trimethyl-5-vinyl-1,3-imidazolidin-4-one (4) was obtained which represents an 86% yield based on complete conversion of the precursor polymer; the estimated conversion based on 54% conversion of the precursor polymer was 66%. The product exhibited the same solubility properties as that described in Example 5.Prominent infrared bands in a KBr pellet occurred at 1194, 1383, 1716, and 2930 cm$^{-1}$.

Example 7

Preparation of poly-1,3-dichloro-5-methyl-5-vinylhydantoin (5)

1.7 grams (0.024 mole) of poly-methyl vinyl ketone prepared as described in Example 5 was dissolved in a mixture of 10 milliliters of dioxane, 10 milliliters of ethanol, and 10 milliliters of distilled water. Then 3.25 grams (0.05 mole) of potassium cyanide and 10 grams (0.104 mole) of ammonium carbonate were added to the mixture in a 300 milliliter Parr model 4841 high-pressure reactor. The mixture was held with stirring at 150° C. for 12 hours. The reactor was cooled to 80° C., opened, and the mixture was poured into 400 milliliters of distilled water. The solid product was removed by suction filtration and washed with near boiling water until the wash water became clear. Upon drying in air, 2.4 grams of the poly-hydantoin product were obtained representing a 71% yield assuming complete reaction of all acetyl moieties. However, infrared and $^{13}$C NMR analyses indicated that some acetyl groups were left unreacted such that a 39% conversion has been estimated. The product exhibited prominent infrared bands in a KBr pellet at 1456, 1725, 1780, 2934, and 3200 cm$^{-1}$; $^{13}$C NMR (DMSO-d$_6$) δ=19, 26, 34, 54, 119, 157, 178, 210.

1.4 grams of the poly-hydantoin prepared as described above were suspended in 20 milliliters of 2 normal sodium hydroxide and chlorinated in the same manner as described in previous examples. 1.65 grams of poly-1,3-dichloro-5-methyl-5-vinylhydantoin (5) which represents a yield of 79%, assuming complete conversion of the original poly-methyl vinyl ketone, was obtained. However, using the 39% estimated conversion rate discussed above, the estimated conversion to final product was 66%. The product exhibited the same solubility properties as did the poly-imidazolidinone described in Example 5, except the poly-hydantoin was not soluble in 3 normal sodium hydroxide. Prominent infrared bands at 1123, 1383, 1445, 1744, 1800, and 2949 cm$^{-1}$ were observed for the product in a KBr pellet.

Example 8

Preparation of poly-1,3-dichloro-(4-methylene-6-yl)-4,6-dimethyl-3,4,5,6-tetrahydro(1H)pyrimidine-2-one (7)

A solution of 80 milliliters of 2.4 normal sodium hydroxide was placed in a 250 milliliter flask and cooled to less than 5° C. using a salted ice bath. 9.6 grams (0.06 mole) of liquid bromine was added, and the mixture was stirred for 20 minutes. Polymethacrylamide was prepared by the method of McNeill and Zulfiqar in *J Poly. Sci.*, 16:2645 (1978). 4.25 grams (0.05 mole of repeating unit) of this polymer was added to the mixture which was stirred for 45 additional minutes. The reaction mixture was then held at 70–75° C. under a nitrogen atmosphere for 12 hours. The solution was condensed under reduced pressure to 30 milliliters, and it was added to 400 milliliters of methanol. The solid product was removed by suction filtration, dissolved in 30 milliliters of water, and precipitated using a 400 milliliter portion of methanol. The final product, poly-methyl vinyl amine, was removed by suction filtration and dried under reduced pressure. The yield was 2.5 grams which was 88% of that expected theoretically. Infrared analysis provided prominent bands in a KBr pellet at 866, 1453, and 3279 cm$^{-1}$, with the absence of a band in the carbonyl region as expected.

2.05 grams (0.036 mole of the repeating unit) of the poly-methyl vinyl amine prepared as described above was dissolved in 100 milliliters of 1.33 normal sodium hydroxide in a 500 milliliter flask. To this solution was added 100 milliliters of toluene and 0.08 grams of cetyltrimethylammonium bromide for the purpose of phase-transfer catalysis. The mixture was held with stirring at a temperature of less than 10° C. while phosgene gas was bubbled in until the pH reached 7.0. The aqueous layer containing the desired product was separated from the toluene layer, and the water was removed under reduced pressure. The pale yellow product which resulted was washed with several portions of methanol and dried under reduced pressure. The yield of poly-(4-methylene-6-yl)-4,6-dimethyl-3,4,5,6-tetrahydro(1H) pyrimidine-2-one was 1.20 grams or 48% of that expected theoretically. The product exhibited prominent infrared bands in a KBr pellet at 1386, 1653, 2977, and 3266 cm$^{-1}$.

2.00 grams (0.014 mole of the repeating unit) of the product described above were dissolved in 100 milliliters of 2 normal aqueous sodium hydroxide in a 250 milliliter flask. The solution was stirred at a temperature below 10° C. while chlorine was slowly bubbled in until the pH reached 7.0. A pale yellow solid precipitated which was removed by suction filtration and washed with distilled, deionized water until no free chlorine could be detected analytically in the filtrate. The yield of the product, poly-1,3-dichloro-(4-methylene-6-yl)-4,6-dimethyl-3,4,5,6-tetrahydro(1H) pyrimidine-2-one (7), was 2.23 grams, or 76% of that expected theoretically. The product exhibited prominent infrared bands in a KBr pellet at 1080, 1406, and 1710 cm$^{-1}$.

Example 9

Efficacies of the Poly N-Halamine Compounds Against *Staphylococcus aureus*

Solid samples of the poly N-halamine compounds described in Examples 1–8 were packed into glass Pasteur pipettes (5.75 inches long, 0.25 inches inside diameter) at lengths of 0.5 to 2.0 inches depending upon amount of sample available. The samples were washed with pH 7.0 chlorine-demand-free water until no free chlorine could be detected in the eluted water. Then 1 milliliter of a pH 7.0 aqueous solution of 10$^6$ CFU of *Staphylococcus aureus* (ATCC 6538) was added to the pipette, and the inoculum was allowed to flow through the packed column using gravity feed in most cases. The particle size for some of the polymer samples was sufficiently small that compressed nitrogen was used to force the inoculum through the column to enhance flow rates. The effluent from each sample was collected, and 25 microliter aliquots were removed and plated on nutrient agar. The remaining portions of the effluents were recycled through the columns. This procedure was repeated 5–6 times which allowed for an assessment of biocidal contact times. The plated samples were incubated at 37° C. for 48 hours and then examined for viable growth. Control samples consisted of plating aliquots of the bacterial suspension before passing the bacteria through the biocidal polymer columns, or in some cases, of passing the bacteria through columns containing unchlorinated precursor polymer samples having similar particle sizes. In all cases the two types of control experiments yielded plates which contained confluent growth too numerous to count indicating that the bacterial samples were viable and that the organisms were not simply eliminated by filtration upon passing through the samples. Results are tabulated in Table I.

The data in Table 1 demonstrate that all of the N-halamine biocidal polymers tested were effective at inactivating *S. aureus*. The polymers in classes 1 and 2 were particularly effective even following long time periods of storage at room temperature.

TABLE I

Biocidal Effects of the N-Halamine Polymers

| Polymer[a] | Mesh Size | Column Length (inches) | Age (Days)[b] | Contact time for 6-Log Inactivation of *S. aureus* (min)[c] |
|---|---|---|---|---|
| 1a | 35–60 | 2.0 | 21 | <1.37 |
| 1a | 35–60 | 2.0 | 354 | <1.97 |
| 1b | 25–60 | 2.0 | 14 | 0.90–1.72 |
| 1b | 25–60 | 2.0 | 477 | 2.07–3.03 |
| 2a | 25–60 | 1.0 | 29 | <0.48 |
| 2b | 25–60 | 1.0 | 34 | <0.38 |
| 3 | >45 | 2.0 | 4 | <2.83 |
| 3 | >45 | 2.0 | 86 | 6.40–8.57 |
| 4 | >45 | 1.0 | 6 | 1.24–15.8 |
| 4 | >45 | 0.8 | 113 | 39.7–45.6 |
| 5 | >45 | 2.0 | 7 | <3.00 |
| 5 | >45 | 2.0 | 168 | 4.71–6.59 |
| 5 | >45 | 2.0 | 225 | >16.2[d] |
| 7 | —[e] | 0.5 | 3 | <4.40 |

[a]1a = poly-1,3-dichloro-5-methyl-5-(4'-vinylphenyl)hydantoin
1b = poly-1,3-dichloro-5-methyl-5-(4'-isopropenylphenyl)hydantoin
2a = poly-1,3,5-trichioro-6-methyl-6-(4'-vinylphenyl)-1,3,5-triazine-2,4-dione
2b = poly-1,3,5-trichloro-6-methyl-6-(4'-isopropenylphenyl)-1,3,5-triazine-2,4-dione
3 = poly-1,3-dichloro-2,5,5-trimethyl-2-vinyl-1,3-imidazolidin-4-one
4 = poly-1,3-dichloro-2,2,5-trimethyl-5-vinyl-1,3-imidazolidin-4-one
5 = poly-1,3-dichloro-5-methyl-5-vinylhydantoin
7 = poly-1,3-dichloro-(4-methylene-6-yl)-4,6-dimethyl-3,4,5,6-tetrahydro (1H)-pyrimidine-2-one.
[b]Time in days elapsing between sample synthesis and biocidal test run with storage at room temperature.
[c]Contact times denoted as "<" mean 6-log inactivation during first aliquot; ranges indicate some bacterial growth at first contact time indicated but none by the second indicated.
[d]3 CFU per milliliter detected after longest contact time studied.
[e]Wide distribution of particle sizes used.

Example 10
Long-term Disinfection Efficacy of Polymer 1a 3.32 grams of polymer 1a (poly-1,3-dichloro-5-methyl-5-(4'-vinylphenyl)hydantoin was packed into glass tubing 12 inches long and 0.5 inch inside diameter (ca. 4 inch length of polymer). The glass tube contained a stopcock at the bottom to allow control of exit flow rates. A 2500 milliliter reservoir was connected to the top of the glass tube by Tygon tubing containing an adjustable clamp to control inlet flow rates. The reservoir was filled periodically with pH 7.0 chlorine-demand-free water containing 10$^6$ CFU per milliliter of *Staphylococcus aureus* (ATCC 6538) and stirred continuously at ambient temperature. The solution containing the bacteria was allowed to pass through the column over a period of 31 days. The flow was generally interrupted during nights and holidays, but a total of 6660 milliliters of bacterial solution was used. Occasionally the column was washed with demand-free water to enhance flow rates (a total of 7450 milliliters). The flow rate was difficult to control, but was maintained in the range 6 to 55 seconds per drop. The effluent from the column was periodically tested for viable bacteria. Generally, a 6-log reduction in *S. aureus* was obtained, but occasionally viable bacteria were found, particularly following interruptions in flow through the column.

After the 31 day period, the column was judged to be no longer effective in inactivating bacteria, as the effluents tested provided confluent growth on nutrient agar plates. It was assumed that the N—Cl moieties on the polymer had been inactivated. Then the column was exposed to flowing water containing free chlorine at a concentration of 200 to 460 milligrams per liter. The flow was continued intermittently over a period of 4 days until the effluent contained approximately the same concentration of free chlorine as the reservoir. At this point it was assumed that the N—Cl moieties on the polymer had been regenerated. It was found at this point that the polymer column was again effective at causing a 6-log reduction of *S. aureus* even at flow rates as high as 16 milliliters per minute.

Thus, the N-halamine polymer 1a was effective at killing *S. aureus* flowing through it in aqueous solution over a lengthy period (31 days). Once the polymer was inactivated, it could be regenerated by flowing an aqueous solution of free chlorine through it.

Example 11
Disinfection efficacy of polymer 1a in the presence of filler materials In a manner similar to that described in Example 9 small Pasteur pipettes (5.75 inches long, 0.25 or 0.31 inch inside diameter) were packed with mixtures of poly-1,3-dichloro-5-methyl-5-(4'-vinylphenyl)hydantoin (1a) and a filler material. Those filler materials used included animal charcoal (0.25 grams 1a, 0.25 gram charcoal; 0.25 gram 1a, 2.5 grams charcoal) and sea sand (0.25 gram 1a, 0.50 gram sand; 0.25 gram 1a, 0.75 gram sand; 0.25 grams 1a, 1.25 grams sand; 0.25 gram 1a, 2.50 grams of sand). The dry filler materials were sterilized at 150° C. for 2 hours before packing the pipettes. In each case a 1 milliliter pH 7.0 aqueous inoculum of $10^6$ CFU Staphylococcus aureus (ATCC 6538) was added to the column and allowed to flow through it using gravity feed. The effluents were recycled through the column several times with 25 microliter aliquots of each pass plated on nutrient agar. The plates were incubated at 37° C. for 48 hours. Results are tabulated in Table II.

The data in Table II demonstrate that polymer 1a was effective at inactivating S. aureus even when diluted by a filler material, particularly when the filler material was sea sand. The 10:1 dilution with sea sand provided the most rapid flow rate and was effective in providing a 6-log reduction in S. aureus with only one pass through the column.

TABLE II

Biocidal Effects of Polymer 1a[a] Mixed with Filler Material

| Filler Material | Grams 1a | Grams Filler | Column Length (inches) | Contact Time for 6-Log Inactivation of S. aureus (min)[b] |
|---|---|---|---|---|
| Animal Charcoal | 0.25 | 0.25 | 0.50[c] | >10.48 |
| Animal Charcoal | 0.25 | 2.50 | 2.88[d] | >8.85 |
| Sea Sand | 0.25 | 0.50 | 1.50[c] | <5.80 |
| Sea Sand | 0.25 | 0.75 | 1.88[c] | <6.83 |
| Sea Sand | 0.25 | 1.25 | 2.38[c] | <4.00 |
| Sea Sand | 0.25 | 2.50 | 1.50[d] | <1.88 |

[1a]= poly-1,3-dichloro-5-methyl-5-(4'-vinylphenyl)hydantoin
[b]Contact times denoted as "<" means 6-log inactivation with first aliquot; contact times denoted as ">" mean reduction in viable organisms, but incomplete inactivation by last aliquot (5 passes through the column).
[c]The inside diameter of the column was 0.25 inch.
[d]The inside diameter of the column was 0.31 inch.

Example 12
Biocidal Efficacy of Polymer 1a Against Microorganisms Found in Potable Water Systems on Spacecraft The biocidal efficacy of poly-1,3-dichloro-5-methyl-5-(4'-vinylphenyl)hydantoin (1a) against microorganisms which are potential pathogens in potable water on spacecraft during long-term missions was evaluated. The species tested were Pseudomonas cepacia (a gram negative rod), Klebsiella pneumoniae (a gram negative rod that forms capsules), Staphylococcus epidermidis (a gram positive coccus), Methylohacterium radiotolerans (a large gram negative rod that forms vacuoles), and Bacillus thuringiensis (a gram positive rod that forms endospores). The objective was to determine the ability of a column of 1a to reduce the viability of microorganisms in flowing water from $10^5$ CFU per milliliter to less than 1 CFU per 100 milliliters.

One gram of the polymer 1a was loaded into a chromatography column and washed thoroughly with distilled, deionized water. 250 milliliter aqueous solutions (phosphate buffered) of each of the organisms containing $10^5$ CFU per milliliter were prepared. Each solution was passed through the column in turn using gravity feed. The inlet inoculum solutions and the effluent solutions were analyzed for viable organisms using both epifluorescent counts and heterotrophic plate counts on R2A (membrane filtration and incubation at 28° C. for 7 days). The flow rates of the inocula were approximately 1.25 milliliters per minute. The column was washed with a 100 milliliter portion of distilled, deionized water after each new organism was passed through it. The wash water effluents were also analyzed for viable organisms. Results are tabulated in Table III.

The data in Table III illustrate that polymer 1a was very effective in inactivating microorganisms which are potential problem pathogens in potable water on spacecraft. There was no significant difference between the epifluorescent counts of total viable and nonviable cells at the inlet and exit of the column for all of the species tested except M. radiololerans. This shows that the column was not simply acting as a filter, although some filtering action may have resulted for the M. radiotolerans as might have been expected since it is a very large gram negative rod (twice as wide as Pseudomonas species). The B. thuringiensis was the most resistant organism to the polymer, probably because it forms resistant endospores. However, increasing the contact time with the polymer should lead to complete inactivation of this organism as well. Polymer 1a should be an excellent biocidal treatment system for environmental control and life support water systems.

TABLE III

Biocidal Effects of Polymer 1a for Potable Water

| Organism | Flow-rate (ml/min) | Epifluorescent cells/ml inlet | Epifluorescent cells/ml exit | Viable CFU/mL inlet | Viable CFU/ 100 mL exit[a] | Viable CFU/ 100 mL exit[b] |
|---|---|---|---|---|---|---|
| P. cepacia | 1.28 | $1.3 \times 10^5$ | $1.6 \times 10^5$ | $6.5 \times 10^4$ | 0 | 0 |
| K. pneumoniae | 1.25 | $3.3 \times 10^5$ | $4.8 \times 10^5$ | $4.0 \times 10^5$ | 0 | 0 |
| S. epidermidis | 1.11 | $9.6 \times 10^5$ | $1.2 \times 10^6$ | $2.8 \times 10^4$ | 0 | 0 |
| M. radiotolerans | 1.28 | $3.8 \times 10^5$ | $3.3 \times 10^4$ | $6.8 \times 10^5$ | 0 | 1 |
| B. thuringiensis | 1.28 | $1.1 \times 10^5$ | $9.6 \times 10^4$ | $2.8 \times 10^2$ | 45 | 8 |

1a = poly-1,3-dichloro-5-methyl-5-(4'-vinylphenyl)hydantoin
[a]From 250 milliliter inocula samples.
[b]From 100 milliliter rinse samples.

Example 13
Leaching of Impurities Into Water Exposed to Polymer 1a

Five portions of 18.3 Megohm distilled, deionized water (100 milliliters each) were passed through a chromatography column containing 1 gram of poly-1,3-dichloro-5-methyl-5-(4'-vinylphenyl)hydantoin at a flow rate of approximately 1.5 milliliters per minute. Each fraction of effluent was then analyzed for total organic carbon (TOC), free chlorine, total chlorine, chloride anion, nitrate anion, and sulfate anion. A standard gas chromatography/mass spectrometry volatile organic analysis (VOA) was also performed. Results are tabulated in Tables IV and V.

The data from Tables IV and V indicate that the leaching rates of impurities from polymer 1 a were not continuous. In fact, the rates declined as additional volumes of water were flowed through the column indicating that the impurities were being removed by the washing process. The concentration levels of the impurities are below the level of concern for potable water disinfection. For example, the trihalomethane chloroform appeared at levels well below the regulatory guideline of 100 parts per billion. Thus it can be concluded that polymer 1a would not pose a health threat to humans or animals drinking water disinfected by it.

TABLE IV

Leachate Analysis for Polymer 1a Exposed to Pure Water

| Fraction Number[a] | TOC ppm[b] | Chlorine, ppm | | Anions, ppm | | |
|---|---|---|---|---|---|---|
| | | Free | Total | Cl$^-$ | NO$_3^-$ | SO$_4^{-2}$ |
| 1 | 1.15 | 0.98 | 1.62 | 2.84 | 0.38 | 0.59 |
| 2 (overnight)[c] | 0.72 | 0.23 | 0.7 | 1.26 | 0.35 | 0.54 |
| 3 | 0.99 | 0.16 | 0.71 | 1.98 | 0.39 | 0.53 |
| 4 (over weekend)[c] | 0.55 | 0.13 | 0.45 | 0.43 | 0.17 | 0.16 |
| 5 | 0.51 | 0.12 | 0.16 | 0.33 | 0.14 | ND[d] |

[a]100 milliliter fractions of distilled, deionized water flowed through column.
[b]Total organic carbon in parts per million.
[c]Interruption of flow for the period indicated.
[d]No determination.
1a = poly-1,3-dichloro-5-methyl-5-(4'-vinylphenyl)hydantoin.

TABLE V

Leachate Analysis of Volatile Organics for Polymer 1a Exposed to Pure Water

| Fraction Number[a] | Oranic Component | Amount, ppb[b] |
|---|---|---|
| 1 | 2-Butanone | 30 |
| | Chloroform | 15 |
| | Methylene Chloride | 7 |
| 2 | 2-Butanone | 23 |
| | Chloroform | 11 |
| (overnight)[c] | | |
| 3 | Chloroform | 16 |
| 4 | 2-Butanone | 16 |
| | Chloroform | 9 |
| (over weekend)[c] | | |
| 5 | 2-Butanone | 45 |
| | Methylene Chloride | 8 |

[a]milliliter fractions of distilled, deionized water flowed through Column.
[b]Concentration of volatile organics in parts per billion.
[c]Interruption of flow for the period indicated.
1a = poly,1,3-dichloro-5-methyl-5-(4'-vinylphenyl)hydantoin.

Example 14
Exposure of Polymer 1a to Water at Different pHs, Temperatures, and Containing Chlorine Demand Pasteur pipettes containing poly-1,3-dichloro-5-methyl-5-(4'-vinylphenyl)hydantoin (1a) to a length of 1 inch (0.25 inch inside diameter) were exposed to pH 4.5 demand-free water, pH 9.5 demand-free water, pH 7.0 demand-free water at 37° C., water containing heavy chlorine demand, 0.02 normal sodium thiosulfate solution, and ethanol. In each case the column was washed with the solution until no free chlorine could be detected in the effluent. Then generally the column was exposed to 1 milliliter of an inoculum containing 10$^6$ CFU of either *Staphylococcus aureus* (ATCC 6538) or *Salmonella enteritidis* (ATCC 13706), and the inoculum was flowed through the column using gravity feed in several passes with 25 microliter aliquots being plated on nutrient agar after each pass. The plates were incubated at 37° C. for 48 hours and then assessed for viable bacteria.

In the cases of pH 4.5 and pH 9.5 water, the column was exposed to ten 1 milliliter inocula of *S. aureus* with intermittent exposure to 100 milliliter portions of buffered demand-free water. No viable bacteria were ever detected showing that mild acid and alkaline waters do not adversely affect the polymer 1a.

In the case of the 37° C. hot water wash only one inoculum of *S. aureus* was used following continuous flow of the hot water until no free chlorine could be detected in the effluent. Again, no viable bacteria were detected, even after only one pass through the column (contact time 1.37 minutes). This result indicates that polymer 1a may be useful for disinfection of hot water such as in hot tubs and shower lines.

To test the effect of chlorine demand, a water sample was prepared containing 375 milligrams per liter of each of the inorganic salts sodium chloride, potassium chloride, calcium chloride, and magnesium chloride; 50 milligrams per liter of Bentonite clay; 30 milligrams per liter of humic acid, 0.01 percent final concentration of heat-treated horse serum; and 5×10$^5$ cells per milliliter of heat-killed *Saccharomyces cerevisiae* yeast cells; the water was buffered to pH 9.5. A column containing polymer 1a was exposed to 1 milliliter of the water sample described above and then 1 milliliter of *S. enteritidis* in several cycles in the usual fashion. The process was repeated four more times with the same column. Although the flow time in the column rose to about 20 minutes during the course of the experiment due to plugging from the matter in the water sample, no viable bacteria were ever detected. This indicates that polymer 1a is resistant to deactivation by heavy chlorine demand from organic materials.

A column receiving 1 milliliter of 0.02 normal sodium thiosulfate solution was not able to kill *S. enteritidis* showing that this reducing agent reacted with the N—Cl moieties to deactivate them. However, the column could be regenerated following treatment with sodium thiosulfate by flowing aqueous free chlorine through it. Likewise, a 5 milliliter portion of ethanol rendered the polymer in a column almost inactive. It is suspected that alcohols may protonate the nitrogen moieties which contain chlorine.

Example 15
Polymer 1a Zone of Inhibition Studies

Zone of inhibition studies were performed for dry solid poly-1,3-dichloro-5-methyl-5-(4'-vinylphenyl)hydantoin (1a). Shallow 0.25 inch diameter holes were drilled in Tryptic Soy agar plates with the bottom of each hole being sealed by a drop of melted agar. The plates were inoculated with a given bacterium or fungus, including *Staphylococcus aureus* (ATCC 6538), *Pseudomonas aeruginosa* (ATCC 27853), *Escherichia coli* (ATCC 2666), *Salmonella enteritidis* (ATCC 13076), *Salmonella typhimurium* (ATCC 6994), *Shigella boydii* (ATCC e9207), *Candida albicans* (ATCC 44506), and *Rhodoturula rubra* (ATCC 16639). Immediately following inoculation of the plates, the holes were filled with 50 milligrams of dry polymer 1a and incubated for 24 hours at 37° C. The zones of inhibition were measured using a Fisher-Lilly Antibiotic Zone Reader. The results are tabulated in Table VI.

TABLE VI

Zones of Inhibition of Polymer 1a for Various Organisms

| Organism | Zone in mm[a] |
| --- | --- |
| Staphylococcus aureus | 36.2 |
| Pseudomonas aeruginosa | 20.0 |
| Escherichia coli | 25.2 |
| Salmonella enteritidis | 33 6 |
| Salmonella typhimurium | 30.2 |
| Shigella boydii | >50 |
| Candida albicans | 22.0 |
| Rhodoturula rubra | 18.4 |

[a]Diameter in millimeters caused by 50 milligrams of polymer 1a in a 0.25 inch diameter well.
1a = poly-1,3-dichloro-5-methyl-5(4'-vinylphenyl)hydantoin.

The data in Table VI demonstrate that solid polymer 1a was effective at inhibiting the growth of a variety of organisms.

Example 16
Use of Polymer 1a in Disinfecting Gas Streams

One inch samples (0.25 inch inside diameter) of poly-1,3-dichloro-5-methyl-5-(4'-vinylphenyl)hydantoin (1a) an loaded into two Pasteur pipettes. An aqueous solution of 125 milliliters of $10^6$ CFU per milliliter of *Staphylococcus aureus* (ATCC 6538) was placed in a 250 milliliter flask containing a two-hole stopper filled with two 0.375 inch diameter glass tubes. One tube extended below the solution level and was connected by Tygon tubing to a laboratory source of nitrogen gas. The other tube which was above the solution level was connected by Tygon tubing to the Pasteur pipet containing dry polymer. Sufficient nitrogen pressure was exerted to create an aerosol of the *S. aureus* organisms. Samples of the aerosol were collected for 2 minutes on rotating nutrient agar plates before and after the polymer columns. The plates were incubated at 37° C. for 48 hours before analyses.

The plates exposed to the aerosol before entrance into the columns yielded confluent bacterial growth (too numerous to count) as did plates exposed to the exit aerosol from the unchlorinated polymer. This indicated that the aerosol was viable with bacteria and that the columns did not remove viable bacteria by mere filtration. The column containing chlorinated polymer 1a, however, yielded 23 CFU immediately after instituting the aerosol flow, 8 CFU five minutes later, and O CFU ten minutes after beginning the flow. Thus polymer 1a was effective at killing *S. aureus* in an aerosol, and it improved with time of flow, probably due to wetting by the aqueous aerosol.

Since polymer 1a, following adequate washing to remove occluded free chlorine, releases very little free chlorine, it will be effective in applications requiring air filtration and disinfection.

Example 17
Use of Polymer 1a as a Preservative Biocide in Paints

Samples of poly-1,3-dichloro-5-methyl-5-(4'-vinylphenyl)hydantoin (1a) were tested for efficacy at preventing biofouling in commercial paint. The paint utilized was Glidden LM2000 containing about 3% by weight kaolin clay, 7.5% diatomaceous silica, 15% titanium dioxide, 3% aluminum hydroxide, 3% amorphous silica, 2.5% acrylic emulsion, and 45% water. The average particle size of polymer 1a suspended in the paint was 32.5 microns, and samples containing 0.5% and 2.0% of polymer 1a were employed. An appropriate control paint sample containing no polymer 1a was also run. The samples were inoculated with 15 microliter aliquots containing Pseudomonas, Citrobacter and Enterobacter species (about $10^5$ cells) and allowed to incubate at 25° C. for 72 hours. The control sample contained 5703 cells per milliliter after 72 hours, while all samples containing polymer 1a showed 0 cells per milliliter. This result indicates that polymer 1a was effective at preventing bacterial contamination in paint for at least 72 hours. The samples containing 2% of 1a had sufficiently high viscosity that gel formation resulted; this was not the case for the samples containing 0.5% of 1a. Polymer 1a should be effective as a preservative at low concentration in paints which do not contain reducing agents such as bisulfites, thiosulfates, etc.

Example 18
Preparation and biocidal efficacy of poly-1,3-dibromo-5-methyl-5-(4'-vinylphenyl)hydantoin 5.0 grams (0.023 mole) of poly-5-methyl-5-(4'vinylphenyl)-hydantoin prepared as described in Example 1 were suspended in 200 milliliters of 0.25 normal sodium hydroxide solution in a 500 milliliter flask held at a temperature below 10° C. Then 8.0 grams (0.05 mole) of liquid $Br_2$ were slowly added from a dropping funnel to the suspension while stirring at a temperature below 10° C. After the addition of bromine was completed, the mixture was stirred for another 30 minutes at 10° C., and the product poly-1,3-dibromo-5-methyl-5-(4'-vinylphenyl)hydantoin was recovered by suction filtration and washing with distilled water, 7.05 grams of product representing an 81% conversion were obtained. The polymer was completely insoluble in water and exhibited prominent infrared bands in a KBr pellet at 1722 and 1789 $cm^{-1}$.

The brominated polymer could also be prepared by reaction of poly-5-methyl-5-(4'-vinylphenyl)hydantoin as prepared in Example 1 with sodium hypobromite solution. The sodium hypobromite solution was prepared by reacting 2.57 grams of sodium bromide with 13.0 grams of 32.18% potassium peroxymonosulfate in 100 milliliters of water. The mixture of polymer and sodium hypobromite was stirred for 1 to 2 hours at 10° C.; 3.23 grams of the light yellow solid product which was poly-1,3-dibromo-5-methyl-5-(4'-vinylphenyl)hydantoin was obtained after suction filtration and washing with distilled water. This represented a 62% conversion to the desired brominated polymer. The brominated polymer could also be prepared by passing an aqueous solution of sodium hypobromite through a column filter containing unhalogenated poly-5-methyl-5-(4'-vinylphenyl)-hydantoin.

In experiments similar to those described in Example 9, the brominated polymer (0.33 grams, 25–60 mesh, in a 1 inch column) provided a 6-log inactivation of the bacterium *S. aureus* in aqueous solution (pH 7.0) in a contact time of less than 2.22 minutes, which was the most rapid flow rate tested. The brominated polymer leached free $Br^+$ into water at a concentration in the range 2.0–2.5 milligrams per liter.

The data in this Example demonstrate that the brominated analog of polymer 1a (see Example 1) is biocidal, and releases a small amount of free bromine into water.

Example 19
Stabilization of and Controlled Release of Free Bromine in the Presence of Ultraviolet Photons A solution of 3 liters of 5.0 milligrams per liter of $Br^+$ was prepared by oxidation of sodium bromide using potassium peroxymonosulfate as the oxidizing agent. This solution was circulated through a column filter containing 1.62 grams of poly-1,3-dibromo-5-methyl-5-(4'-vinylphenyl)hydantoin prepared as described in Example 18 for 24 hours so as to obtain an equilibrium concentration of $Br^+$ in the solution. This solution was then divided into two equal parts, and equal portions (1 liter) were placed into two 1-liter beakers. One beaker was connected as a closed-loop through a Gelman Sciences Posiflo II circulating water pump to the filter containing the brominated polymer. The other beaker was connected through an identical water pump to an identical filter containing 6.50 grams of sterilized sea sand. Both filters were masked from exposure to ultraviolet light, but the reservoirs were exposed to identical ultraviolet photon fluxes provided by the ultraviolet lamp in a Labgard biological safety cabinet. The water containing free bromine was then circulated through the two filters at a flow rate of 50 milliliters per minute, and the ultraviolet source was turned on. Aliquots were withdrawn periodically from each reservoir and analyzed for free bromine content using standard iodometric titrimetry.

The loss processes for $Br^+$ for both reservoirs were found to be first order with rate constants of $4.8 \times 10^{-3}$ $min^{-1}$ for the sand filter and $2.84 \times 10^{-4}$ for the brominated polymer filter. Thus the brominated polymer stabilized the $Br^+$ in the presence of ultraviolet radiation by a factor of 16.9. Also, 1.3 milligrams per liter of $Br^+$ remained in the reservoir connected to the brominated polymer filter after 50 hours' time, while $Br^+$ was completely depleted from the sand-filtered solution after only 8 hours.

In an analogous experiment in which bromochlorodimethyl hydantoin was used as the free bromine source, the relative stabilization in the presence of ultraviolet photons caused by the brominated polymer relative to sand was 10.6.

The data is this Example demonstrate that the brominated polymer stabilizes and controls the release of free bromine in the presence of ultraviolet light. The polymer should thus be of use for this purpose for recreational water applications.

Example 20

Preparation of poly-5methyl-5-(4'-vinylphenyl) hydantoin from the monomer 5-methyl-5-(4'-vinylphenyl)hydantoin A 3.0 gram sample (0.0205 mole of repeating unit) of poly-4-vinylacetophenone prepared as described in Example 1 was placed in a 100 milliliter flask which was connected to a vacuum system. The flask was heated by open flame with the contents at a pressure of 20 millimeters of mercury until a yellow oily liquid was produced which was collected in a 50 milliliter flask through an air-cooled condenser (Kenyon and Waugh, *J. Polymer Science* 32:83–88 (1958). The product (2.70 grams), which was the monomer 4-vinylacetophenone, was produced with a yield of 90.0% of that theoretically expected. $^1H$ NMR ($CDCl_3$ $\delta$=2.58 (s,3H); 5.39(d,1H); 5.86 (d,1H); 6.79 (m,1H); 7.47 (d,2H); 7.91 (d,2H).

A 7.3 gram sample (0.05 mole) of the monomer 4-vinylacetophenone was dissolved in 80 milliliters of 95% ethanol. A solution of 9.0 grams (0.14 mole) of KCN, 28.8 grams (0.3 mole) of $(NH_4)_2CO_3$ in 70 milliliters of water was added to the 4-vinylacetophenone solution in a 250 milliliter flask. The flask was sealed and placed in a water bath which was maintained in the temperature range 60–70° C. After 15 hours of stirring, the flask was cooled to room temperature. The reaction contents were poured into 200 milliliters of 5% HCl solution, and the product, which was 5-methyl-5-(4'-vinylphenyl)hydantoin monomer, was recovered as a white solid by suction filtration. The product was purified by recrystalization from boiling water and was obtained in the amount of 10.19 grams which was 94.4% of that theoretically expected. Properties of the novel monomer are m.p. 184–186° C.; IR (KBr) 1402, 1725, 1775, and 3214 $cm^{-1}$; $^1H$ NMR (DMSO-$d_6$) $\delta$=1.65 (s,3H); 5.28 (d,1H); 5.84 (d,1H); 6.74 (m,1H); 7.47 (m,4H); 8.62 (s,1H); 10.78 (s,1H).

A 2.0 gram sample (0.009 mole) of the monomer 5-methyl-5-(4'-vinylphenyl)hydantoin was dissolved in 20 milliliters of absolute ethanol in a 100 milliliter flask. Under a nitrogen atmosphere 0.03 grams ($1.83 \times 10^{-4}$ mole) of AIBN (azobisisobutyronitrile) was added to the flask, and the solution was refluxed for 20 hours. To remove unreacted monomer and other impurities, the solid product was recovered by suction filtration of the hot mixture. The product which was poly-5-methyl-5-(4'-vinylphenyl)hydantoin was washed with two 10 milliliter portions of ethanol and dried at room temperature. The yield was 1.6 grams which was 80% of that expected theoretically. The material could be chlorinated to obtain the same biocidal properties as those for the polymer produced from commercial poly-styrene in Example 1. Its spectroscopic properties were: IR (KBr) 1256, 1402, 1720, 1775, and 3252 $cm^{-1}$; $^{13}C$ NMR (DMSO-$d_6$) $\delta$=18.57, 25–26.5, 63.80, 124–128, 156.3, 177.1.

The data in this Example show that poly-5-methyl-5-(4'-vinylphenyl)hydantoin can be made by polymerization of the monomer hydantoin as well as by modification of commercial polystyrene as described in Example 1.

Example 21

Copolymerization of 5-methyl-5-(4'-vinylphenyl) hydantoin monomer with acrylonitrile A 0.43 gram (0.002 mole) sample of the monomer 5-methyl-5-(4'-vinylphenyl)hydantoin prepared as described in Example 20 and 6.36 grams (0.12 mole) of acrylonitrile were dissolved in 40 milliliters of N,N-dimethylacetamide. Under a nitrogen atmosphere, 0.08 grams ($4.88 \times 10^{-4}$ mole) of AIBN was added to a 100 milliliter flask containing the solution of polymerizable monomers. The mixture was allowed to react for 20 hours at 70–80° C. under a nitrogen atmosphere. At the conclusion of the reaction, the mixture was poured into 300 milliliters of water. A light yellow copolymer product was recovered by suction filtration, and after washing with water, yielded 5.55 grams or 81.7% of that theoretically expected. Spectroscopic properties were: IR(KBr): 1253, 1402, 1454, 1730, 1775, 2244, and 3250 $cm^{-1}$; $^{13}C$ NMR (DMSO-$d_6$) $\delta$=26.7, 27.3, 27.8, 32.5–32.8, 63.7, 120–120.3.

The data in this Example show that the monomer precursor to the poly-styrene hydantoin can be copolymerized with common polymerizable materials such as acrylonitrile. The resulting copolymers, after halogenation of the hydantoin moiety, will be biocidal materials.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A cyclic amine polymer having a monomeric repeating unit comprising one or more structures of the formula I, II, III, IV, V, VI, VII, VIII, IX or X:

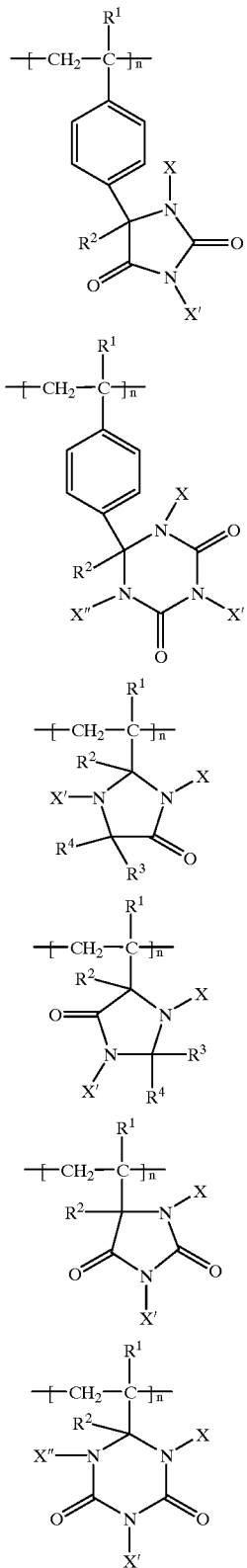

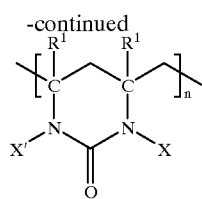

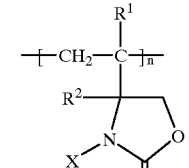

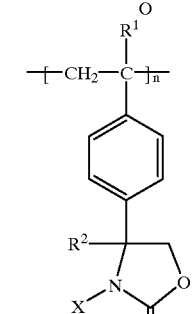

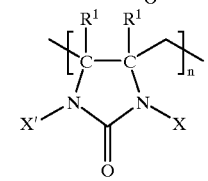

wherein X, X' and X" are hydrogen; $R^1$ is hydrogen or $C_1$ to $C_4$ alkyl; $R^2$ is $C_1$–$C_4$ alkyl, benzyl or $C_1$–$C_4$ alkyl-substituted benzyl; and $R^3$ and $R^4$ are independently $C_1$–$C_4$ alkyl, phenyl, $C_1$–$C_4$ alkyl-substituted phenyl, benzyl or $C_1$–$C_4$ alkyl-substituted benzyl, or $R^3$ and $R^4$ together form a pentamethylene or tetramethylene moiety.

2. The polymer of claim 1, wherein the polymer is a copolymer.

3. The polymer of claim 1, wherein the polymer is a homopolymer.

4. The polymer of claim 1, wherein the monomeric repeating unit consists of one or more structures of the formula I, II, III, IV, V, VI, VII, VIII, IX or X.

5. The polymer of claim 1, further comprising a monomeric repeating unit M different than the monomeric structures of the formula I, II, III, IV, V, VI, VII, VIII, IX and X, wherein the monomer M is copolymerizable with the monomeric structure of the formula I, II, III, IV, V, VI, VII, VIII, IX or X without hindering the ability of the monomeric structure of the formula I, II, III, IV, V, VI, VII, VIII, IX or X of the resultant cyclic amine copolymer to be halogenated.

6. The cyclic amine copolymer of claim 5, wherein the monomeric repeating unit M is one or more of acrylonitrile, styrene, acrylamide, methacrylamide, methyl methacrylate, ethylene, propylene, butylenes, or butadiene.

7. The polymer of claim 1 wherein the polymer is poly-5-methyl-5-(4'-vinylphenyl)hydantoin.

8. The polymer of claim 1 wherein the polymer is poly-5-methyl-5-(4'-isopropenylphenyl)hydantoin.

9. The polymer of claim 1 wherein the polymer is poly-6-methyl-6-(4'-vinylphenyl)-1,3,5-triazine-2,4-dione.

10. The polymer of claim 1 wherein the polymer is poly-6-methyl-6-(4'-isopropenylphenyl)-1,3,5-triazine-2,4-dione.

11. The polymer of claim 1 wherein the polymer is poly-2,5,5-trimethyl-2-vinyl-1,3-imidazolidin-4-one.

12. The polymer of claim 1 wherein the polymer is poly-2,2,5-trimethyl-5-vinyl-1,3-imidazolidin-4-one.

13. The polymer of claim 1 wherein the polymer is poly-5-methyl-5-vinylhydantoin.

14. The polymer of claim 1 wherein the polymer is poly-6-methyl-6-vinyl-1,3,5-triazine-2,4-dione.

15. The polymer of claim 1 wherein the polymer is poly-(4-methylene-6-yl)-4,6-dimethyl-3,4,5,6-tetrahydro(1H)pyrimidin-2-one.

16. The polymer of claim 1 wherein the polymer is poly-4-methyl-4-vinyl-2-oxazolidinone.

17. The polymer of claim 1 wherein the polymer is poly-4-methyl-4-(4'-vinylphenyl)-2-oxazolidinone.

18. A cyclic amine copolymer having a monomeric repeating unit comprising one or more structures of the formula I, II, III, IV, V, VI, VII, VIII, IX or X:

Class I

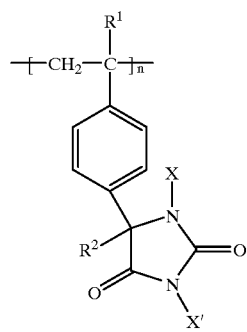

Class II

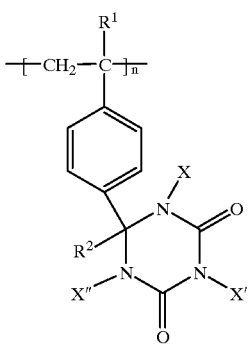

Class III

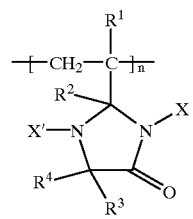

Class IV

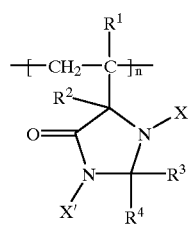

Class V

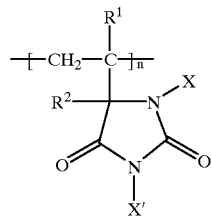

Class VI

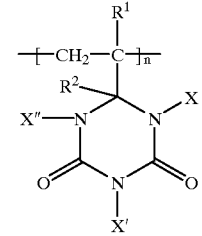

Class VII

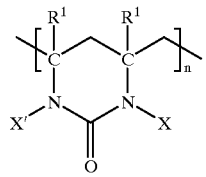

Class VIII

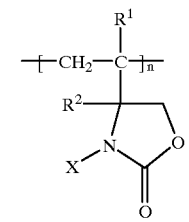

Class IX

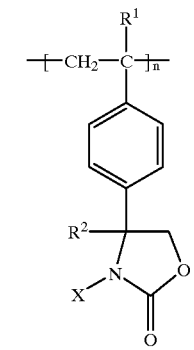

Class X wherein X, X' and X" are independently chlorine, bromine or hydrogen, provided that at least one of X, X' and X" is chlorine or bromine; $R^1$ is hydrogen or $C_1$ to $C_4$ alkyl; $R^2$ is $C_1$–$C_4$ alkyl, benzyl or $C_1$–$C_4$ alkyl-substituted benzyl; and $R^3$ and $R^4$ are independently $C_1$–$C_4$ alkyl, phenyl, $C_1$–$C_4$ alkyl-substituted phenyl, benzyl or $C_1$–$C_4$ alkyl-substituted benzyl, or $R^3$ and $R^4$ together form a pentamethylene or tetramethylene moiety, and further comprising a monomeric repeating unit M different than the monomeric structures of the formula I, II, III, IV, V, VI, VII, VIII, IX and X, wherein the monomer M is copolymerizable with the monomeric structure of the formula I, II, III, IV, V, VI, VII, VIII, IX or X without hindering the ability of the monomeric structure of the formula I, II, III, IV, V, VI, VII, VIII, IX or X of the cyclic amine copolymer to be halogenated.

19. The cyclic amine copolymer of claim 18, wherein the monomeric repeating unit M is one or more of acrylonitrile, styrene, acrylamide, methacrylamide, methyl methacrylate, ethylene, propylene, butylenes, or butadiene.

* * * * *

UNITED STATES PATENT AND TRADEMARK OFFICE
CERTIFICATE OF CORRECTION

PATENT NO.    : 6,294,185 B1
DATED         : September 25, 2001
INVENTOR(S)   : S.D. Worley et al.

It is certified that error appears in the above-identified patent and that said Letters Patent is hereby corrected as shown below:

<u>Title page,</u>
Item [56], References Cited, U.S. PATENT DOCUMENTS, insert in appropriate order: -- 5,490,983 * 2/1996 Worley et al. --

Signed and Sealed this

Thirtieth Day of July, 2002

Attest:

JAMES E. ROGAN
Attesting Officer          Director of the United States Patent and Trademark Office